US012057115B2

(12) United States Patent
Devaraj et al.

(10) Patent No.: US 12,057,115 B2
(45) Date of Patent: Aug. 6, 2024

(54) MESSAGING FROM A SHARED DEVICE

(71) Applicant: Amazon Technologies, Inc., Seattle, WA (US)

(72) Inventors: Christo Frank Devaraj, Seattle, WA (US); Venkata Krishnan Ramamoorthy, Redmond, WA (US); Gregory Michael Hart, Mercer Island, WA (US); Samuel Scott Gigliotti, Seattle, WA (US); Scott Southwood, Seattle, WA (US); Ran Mokady, Seattle, WA (US); Hale Sostock, Seattle, WA (US); Roman Yusufov, Scottsdale, AZ (US)

(73) Assignee: Amazon Technologies, Inc., Seattle, WA (US)

( * ) Notice: Subject to any disclaimer, the term of this patent is extended or adjusted under 35 U.S.C. 154(b) by 302 days.

(21) Appl. No.: 17/146,997

(22) Filed: Jan. 12, 2021

(65) Prior Publication Data
US 2021/0210094 A1   Jul. 8, 2021

Related U.S. Application Data

(63) Continuation of application No. 15/390,944, filed on Dec. 27, 2016, now Pat. No. 10,916,243.

(51) Int. Cl.
*G10L 15/22* (2006.01)
*G10L 13/08* (2013.01)
(Continued)

(52) U.S. Cl.
CPC .............. *G10L 15/22* (2013.01); *G10L 13/08* (2013.01); *G10L 15/1815* (2013.01);
(Continued)

(58) Field of Classification Search
CPC ..... G10L 15/22; G10L 13/08; G10L 15/1815; G10L 17/06; G10L 17/22;
(Continued)

(56) References Cited

U.S. PATENT DOCUMENTS 9,590,941 B1 *   3/2017   Itoh ..................... H04L 51/224
9,621,501 B2 *   4/2017   Lu ....................... H04L 51/224
(Continued)

*Primary Examiner* — Thuykhanh Le
(74) *Attorney, Agent, or Firm* — Pierce Atwood LLP

(57) ABSTRACT

Methods and systems for facilitating communications between shared electronic devices are described herein. In some embodiments, a group account may be assigned to a shared electronic device. The group account may include one or more user accounts, where individuals associated with those user accounts may interact with the shared electronic device, and also may form a part of the group account. When a message is sent from one shared electronic device to another personal device or shared electronic device, the message may be indicated as being sent from the group account, as if the shared electronic device corresponds to its own separate account. In some embodiments, speaker identification processing may be employed to determine a speaker of the message and, if the speaker is able to be identified, the message may be sent from the corresponding speaker's user account instead of the shared electronic device's corresponding group account.

20 Claims, 8 Drawing Sheets

(51) Int. Cl.
*G10L 15/18* (2013.01)
*G10L 17/06* (2013.01)
*G10L 17/22* (2013.01)
*H04L 51/02* (2022.01)
*H04L 51/046* (2022.01)
*H04L 51/10* (2022.01)
*H04L 51/224* (2022.01)
*H04L 51/52* (2022.01)
*H04L 67/104* (2022.01)
*H04L 67/303* (2022.01)
*H04L 67/306* (2022.01)

(52) U.S. Cl.
CPC .............. *G10L 17/06* (2013.01); *G10L 17/22* (2013.01); *H04L 51/02* (2013.01); *H04L 51/046* (2013.01); *H04L 51/224* (2022.05); *H04L 67/1044* (2013.01); *H04L 67/303* (2013.01); *H04L 67/306* (2013.01); *G10L 2015/223* (2013.01); *H04L 51/10* (2013.01); *H04L 51/52* (2022.05)

(58) Field of Classification Search
CPC ... G10L 2015/223; G10L 15/00; H04L 51/02; H04L 51/046; H04L 51/224; H04L 67/1044; H04L 67/303; H04L 67/306; H04L 51/10; H04L 51/52
USPC ......................................................... 704/235
See application file for complete search history.

(56) References Cited

U.S. PATENT DOCUMENTS

| | | | | |
|---|---|---|---|---|
| 9,929,987 B2* | 3/2018 | Bouzid | ................ | G06F 16/972 |
| 10,002,611 B1* | 6/2018 | Typrin | ................ | H04L 51/10 |
| 10,140,973 B1* | 11/2018 | Dalmia | ................ | G06N 7/01 |
| 10,237,317 B2* | 3/2019 | Celinski | ................ | H04M 1/72412 |
| 10,332,513 B1* | 6/2019 | D'Souza | ................ | G10L 15/22 |
| 10,380,208 B1* | 8/2019 | Brahmbhatt | ................ | G06F 16/9535 |
| 10,425,783 B1* | 9/2019 | Caldwell | ................ | H04W 4/14 |
| 10,565,990 B1* | 2/2020 | Polansky | ................ | H04R 1/08 |
| 10,585,485 B1* | 3/2020 | Karakotsios | ................ | G06F 3/0488 |
| 10,645,224 B2* | 5/2020 | Dwyer | ................ | G06F 40/279 |
| 11,086,592 B1* | 8/2021 | Wang | ................ | H04L 51/10 |
| 2003/0135574 A1* | 7/2003 | Burg | ................ | H04L 51/224 709/207 |
| 2003/0147512 A1* | 8/2003 | Abburi | ................ | H04M 3/5307 379/88.22 |
| 2003/0229670 A1* | 12/2003 | Beyda | ................ | G06Q 10/107 709/206 |
| 2005/0058260 A1* | 3/2005 | Lasensky | ................ | G06Q 10/107 379/1.03 |
| 2006/0020677 A1* | 1/2006 | von Koch | ................ | H04L 51/224 709/207 |
| 2008/0317222 A1* | 12/2008 | Griggs | ................ | A61K 9/2054 370/392 |
| 2009/0259472 A1* | 10/2009 | Schroeter | ................ | G10L 13/00 704/260 |
| 2010/0293601 A1* | 11/2010 | Schultz | ................ | H04L 9/3271 726/4 |
| 2011/0022387 A1* | 1/2011 | Hager | ................ | G06Q 10/107 715/752 |
| 2011/0046939 A1* | 2/2011 | Balasaygun | ................ | H04L 45/586 704/E15.003 |
| 2011/0206191 A1* | 8/2011 | Tengler | ................ | H04L 67/02 379/88.17 |
| 2012/0059653 A1* | 3/2012 | Adams | ................ | G10L 15/19 704/243 |
| 2012/0323575 A1* | 12/2012 | Gibbon | ................ | G06F 3/167 704/E17.001 |
| 2013/0097270 A1* | 4/2013 | Plotkin | ................ | H04L 51/224 709/206 |
| 2013/0165086 A1* | 6/2013 | Doulton | ................ | H04L 51/10 455/414.4 |
| 2013/0346337 A1* | 12/2013 | O'Donnell | ......... | G06Q 10/0833 705/333 |
| 2015/0074771 A1* | 3/2015 | Goldberg | ................ | H04L 63/104 726/4 |
| 2015/0148084 A1* | 5/2015 | Arkko | ................ | H04M 1/645 455/466 |
| 2015/0149179 A1* | 5/2015 | Korbecki | ................ | G10L 13/00 704/260 |
| 2015/0222572 A1* | 8/2015 | Vendrow | ................ | H04L 51/02 715/752 |
| 2015/0317979 A1* | 11/2015 | Yang | ................ | G10L 17/22 704/235 |
| 2015/0365359 A1* | 12/2015 | Hasan | ................ | H04L 51/04 709/206 |
| 2015/0381533 A1* | 12/2015 | Klemm | ................ | H04L 51/02 709/206 |
| 2016/0043979 A1* | 2/2016 | Stern | ................ | H04L 67/125 709/206 |
| 2016/0050177 A1* | 2/2016 | Cue | ................ | H04L 67/1095 709/206 |
| 2016/0071519 A1* | 3/2016 | Hoffmeister | ............ | G10L 15/30 704/232 |
| 2016/0150350 A1* | 5/2016 | Ingale | ................ | H04W 4/38 370/255 |
| 2016/0155443 A1* | 6/2016 | Khan | ................ | G06F 3/167 704/275 |
| 2016/0191453 A1* | 6/2016 | Thomas | ................ | H04L 51/226 709/206 |
| 2016/0275952 A1* | 9/2016 | Kashtan | ................ | G10L 17/00 |
| 2016/0277368 A1* | 9/2016 | Narayanaswamy | ................ | G06F 21/6209 |
| 2016/0277903 A1* | 9/2016 | Poosala | ................ | G06F 3/0488 |
| 2016/0352664 A1* | 12/2016 | Braines | ................ | G06F 3/04842 |
| 2016/0352895 A1* | 12/2016 | Son | ................ | H04L 51/063 |
| 2017/0026333 A1* | 1/2017 | Pitroda | ................ | H04L 51/046 |
| 2017/0149708 A1* | 5/2017 | Baumgartner | .......... | H04L 67/06 |
| 2017/0154626 A1* | 6/2017 | Kim | ................ | G10L 15/22 |
| 2017/0221478 A1* | 8/2017 | Yardley | ................ | G10L 17/00 |
| 2017/0230495 A1* | 8/2017 | Gupta | ................ | H04M 1/2748 |
| 2017/0249291 A1* | 8/2017 | Patel | ................ | H04L 51/063 |
| 2017/0270916 A1* | 9/2017 | Prokhorov | ................ | G10L 15/26 |
| 2017/0310811 A1* | 10/2017 | Zhong | ................ | G06F 3/0485 |
| 2017/0339534 A1* | 11/2017 | Bhalla | ................ | H04W 4/08 |
| 2017/0353416 A1* | 12/2017 | Brooks | ................ | H04L 51/04 |
| 2018/0007210 A1* | 1/2018 | Todasco | ................ | H04M 3/53366 |
| 2018/0034961 A1* | 2/2018 | Engelke | ................ | H04M 1/2475 |
| 2018/0054414 A1* | 2/2018 | LeVasseur | ............ | G06Q 10/10 |
| 2018/0115631 A1* | 4/2018 | Martin | ................ | H04L 67/306 |
| 2018/0152462 A1* | 5/2018 | Steinbach | ............. | H04L 63/123 |
| 2018/0184286 A1* | 6/2018 | Patterson | ............. | H04W 12/02 |
| 2019/0074017 A1* | 3/2019 | Guevara | ................ | G10L 17/20 |
| 2019/0080697 A1* | 3/2019 | Grancharov | ........... | G10L 15/26 |
| 2019/0286799 A1* | 9/2019 | Miyazaki | ........... | G06F 16/2477 |
| 2019/0311721 A1* | 10/2019 | Edwards | ................ | G10L 17/06 |
| 2020/0143814 A1* | 5/2020 | Moniz | ................ | G10L 17/06 |
| 2023/0223004 A1* | 7/2023 | Korbecki | ................ | G10L 13/00 704/260 |
| 2023/0267935 A1* | 8/2023 | Guevara | ................ | G10L 17/04 704/246 |

* cited by examiner

| DEVICE IDENTIFIER | GROUP ACCOUNT IDENTIFIER | USER ACCOUNT IDENTIFIER | DEVICE TYPE |
|---|---|---|---|
| 111.xxx | 111.yyy | — | SHARED |
| 222.xxx | 111.yyy | 222.zzz | NON-SHARED |
| 333.xxx | 111.yyy | 333.zzz | NON-SHARED |
| 111.aaa | 111.bbb | — | SHARED |
| 222.aaa | 111.bbb | 222.ccc | NON-SHARED |
| 333.aaa | 111.bbb | 333.ccc | NON-SHARED |
| ZZZ.777 | ZZZ.888 | ZZZ.999 | NON-SHARED |

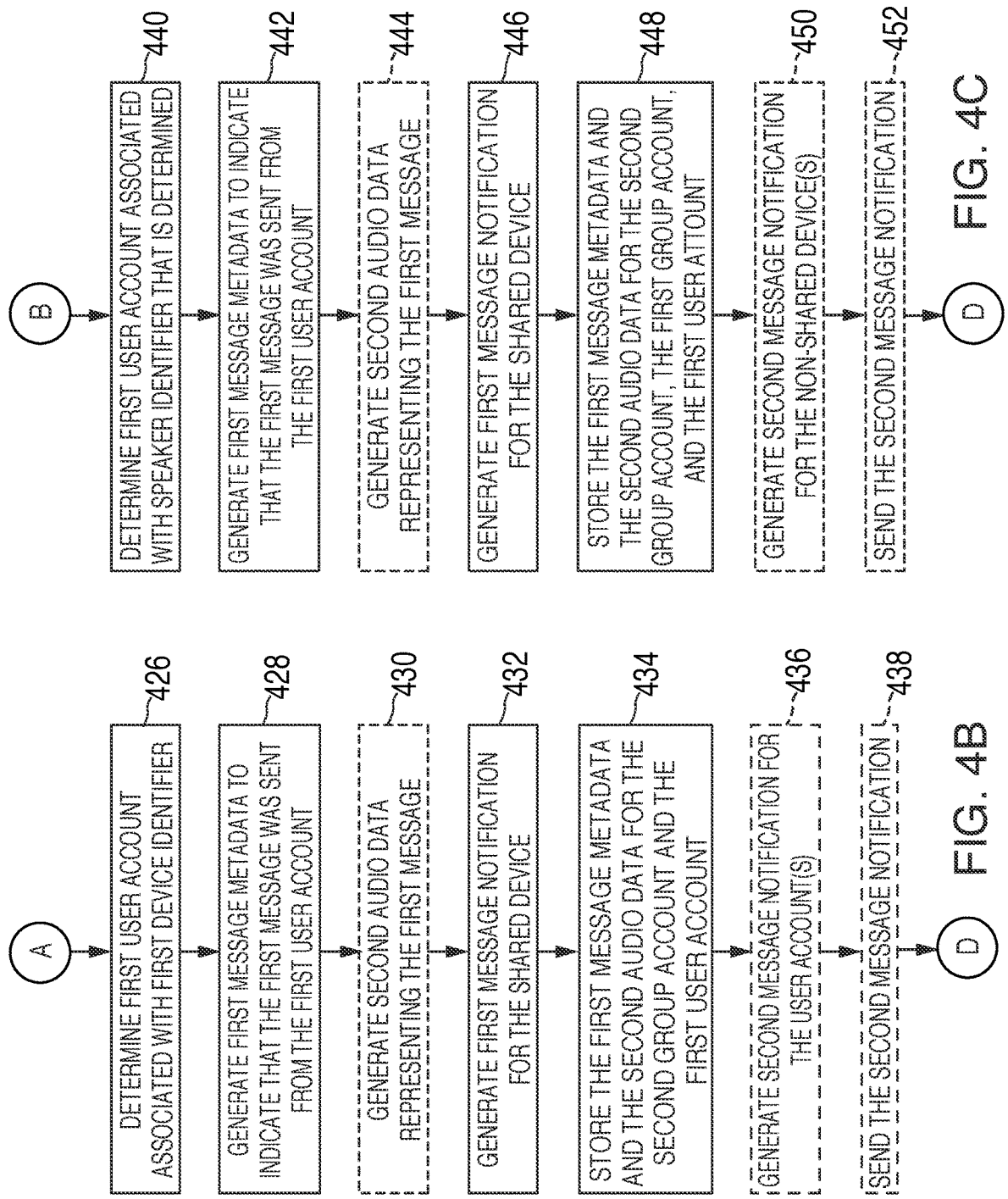

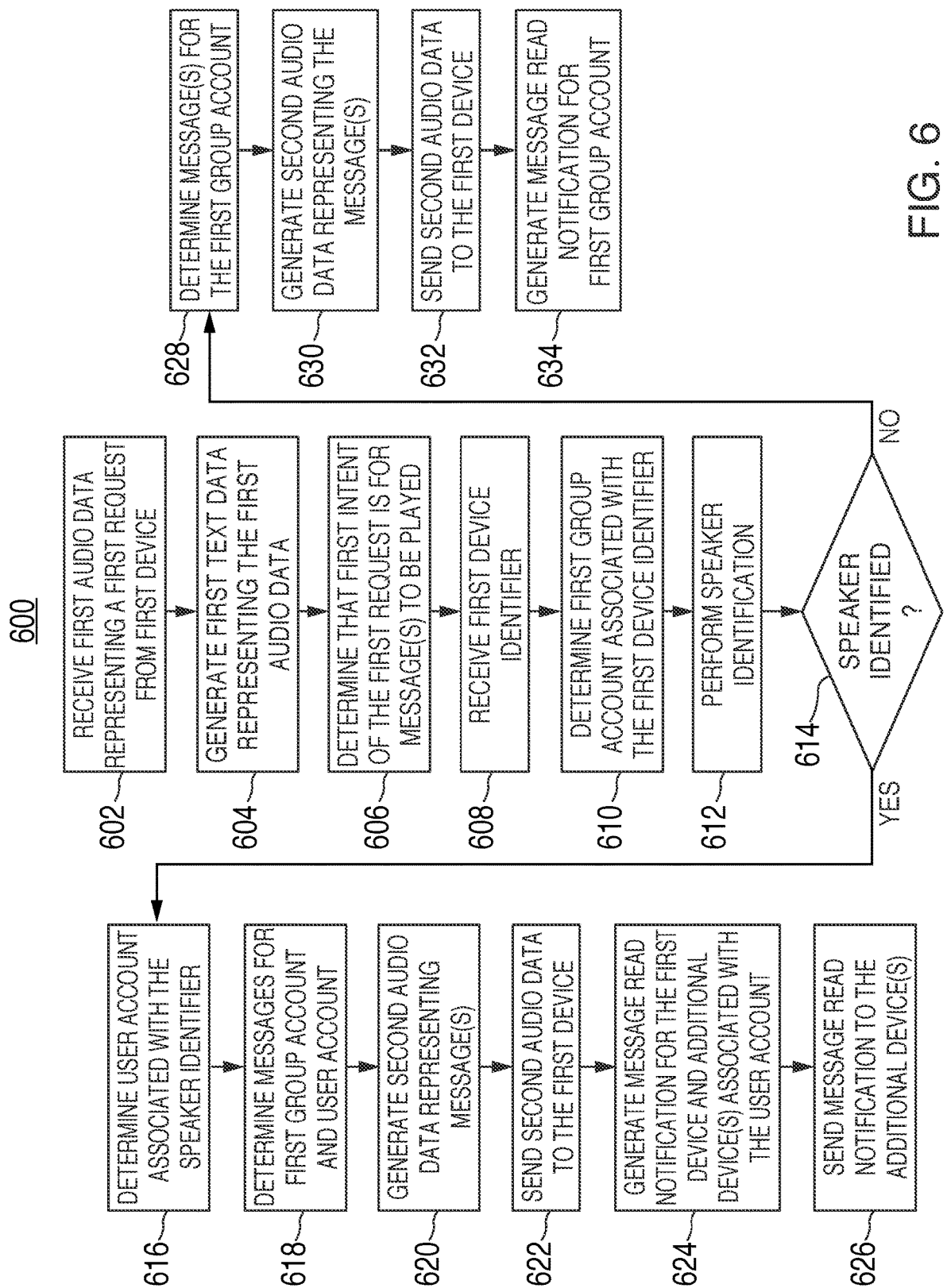

MESSAGING FROM A SHARED DEVICE

CROSS REFERENCE TO RELATED APPLICATION

This application is a continuation of, and claims priority to U.S. Non-provisional patent application Ser. No. 15/390,944, filed on Dec. 27, 2016, and entitled "MESSAGING FROM A SHARED DEVICE," and which is scheduled to issue. The contents of which are expressly incorporated herein in its entirety.

BACKGROUND

Electronic devices are being used more and more with each passing day. Some electronic devices are capable of being used by multiple users. For instance, a shared electronic device may be used by many different individuals, such as members of a same family where the shared electronic device is located, to facilitate the various needs and requests of these individuals.

BRIEF DESCRIPTION OF THE DRAWINGS

FIG. 3 is an illustrative diagram of an exemplary communications table, in accordance with various embodiments;

FIGS. 4A-D are illustrative flowcharts of an exemplary process for sending a message from a first device to a second device, in accordance with various embodiments;

FIG. 6 is an illustrative flowchart of an exemplary process for causing messages to be output from a first device, in accordance with various embodiments.

DETAILED DESCRIPTION

Figure 1:
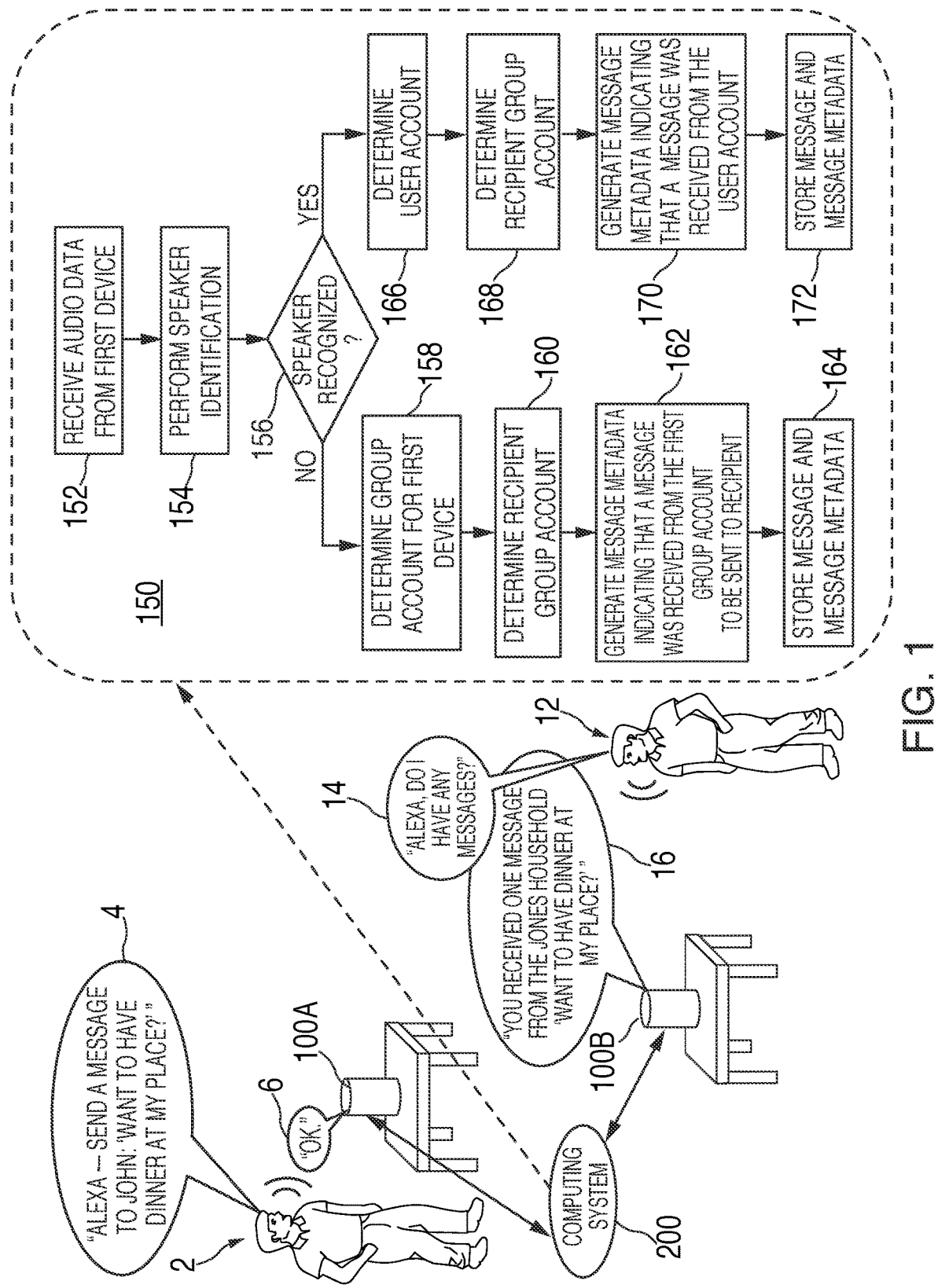
FIG. 1 is an illustrative diagram of an exemplary system for sending a message from one shared electronic device to another shared electronic device, in accordance with various embodiments.

The present disclosure, as set forth below, is generally directed to various embodiments of methods and systems for sending and receiving communications using communal devices. In some embodiments, various types of communications may include, but are not limited to, audio communications, video communications, image communications (e.g., pictures, graphics interchange format ("GIF")), text communications, informational messages (e.g., hyperlinks, files, etc.), and/or any combination thereof, or any other additional type of communication. Such communications, which may also, in some embodiments, be referred to as messages, may be sent from one device to one or more additional devices.

Many households, offices, residences, and/or any other space, may include one or more shared devices. For example, a household may include one or more voice activated electronic devices. As described herein, a "shared device," a "communal device," and/or a "multi-user device" may correspond to various types of electronic devices that are capable of being used by multiple individuals, and, in particular, may be configured to be interacted with by multiple individuals. Voice activated electronic devices, sound activated electronic device, and/or manually activated electronic devices may all correspond to exemplary types of shared devices. An individual located proximate to such a shared device, for example, may be capable of interacting with the shared device either via voice, sound, and/or physical input, depending on the particular device's capabilities and configuration. For example, voice activated electronic devices may be used by one or more individuals to facilitate a plethora of actions, such as, and without limitation, outputting content, obtaining information, interacting with additional devices/systems, and/or communicating with other individuals. As an illustrative example, an individual may use their voice activated electronic device to play music, order food, obtain weather information, and/or send a message to a friend or family member.

Each shared electronic device may be in communication with a communications system, capable of facilitating communications between two or more devices. To identify who is sending a particular message, and who is to be receiving that particular message, an identifier unique to the initiating and recipient device may be used for routing the communications. For instance, a shared electronic device may have a unique device identifier that allows the communications system to identify a corresponding group account that that shared electronic device was assigned to. After receiving the device identifier, a corresponding group account identifier, indicating the group account, may be obtained. This group account may have a name, handle, and/or other type of identifier, that may indicate to recipients of the sent message an identity of the sender. For example, a first individual may send a communication to a second individual using a first shared electronic device. The first shared electronic device may have a first device identifier, which may be linked to a first group account with which the first individual is a member. Using a contact list associated the first group account, the second individual may be identified as a target of the communication, and a second group account associated with the second individual, as well as a second shared electronic device that the second group account is assigned to, may be determined. The second shared electronic device may then receive the communication for consumption by the second individual, or any other individual associated with the second shared electronic device. In some embodiments, the communications system may further indicate to the second individual that the communication was sent from a first group account associated with the first shared device. For example, a message to be sent to another individual may be prefaced by an introductory message indicating that the sender was the first group account—"You received one message from the Smith Family."

In some embodiments, speaker identification processing may be performed to determine, or attempt to determine, a speaker of a communication directed to another individual. Using the example above, speaker identification processing may be performed to the first communication. If the speaker identification processing determines that a speaker identifier, such as a voice print, of the communication corresponds to first voice biometric data associated with the first individual's user account, then the message, when received by the second individual, may be indicated as being sent from the first individual's user account. For example, a message to be sent to another individual may be prefaced by an introductory message indicating that the sender is the first individual's user account—"You received one message from John Smith." However, if the speaker identification processing is unable to determine the speaker of the message, then the communication may be indicated as having been sent from the first group account, as described above.

In addition to sending a message to a targeted individual, or individuals, device, notifications may be sent to other non-shared devices, which may be referred to as personal devices, assigned to user accounts associated with the recipient's group account. For instance, a group account may be generally linked to a shared device, and the group account may be associated with one or more user accounts. Each user account may correspond to an individual that is also associated with the group account. For instance, a user account associated with a group account may be capable of accessing messages, calls, or any other type of communication, that the group account received. As an illustrative example, a family may have a voice activated electronic device, which may be associated with the family's group account. Each family member may have their own user account that is capable of operating under the parameters of the family group account. In some embodiments, personal devices (e.g., devices associated with a particular individual's user account), may also be provided with a notification each time a message, or more generally a communication, is received by the group account. For instance, using the example above, if the second individual also has a personal device linked to their user account, which may also be associated with the second individual's group account, then in response to receiving the message at the second individual's shared device, a notification may also be sent to the personal device indicating that a new message has been received.

Furthermore, in some embodiments, a group account may, itself, include one or more additional group accounts. For example, a first group account may be assigned to a first shared electronic device. The first group account may also include a second group account, which is assigned to a second shared electronic device, but may also be associated with the first group account. As an illustrative example, a first voice activated electronic device may be located within a first room of a household. That first voice activated electronic device may have a first group account with which it is assigned to. A second voice activated electronic device located in a second room of the same household. That second voice activated electronic may have a second group account that is assigned to it, and, at the same time, also being part of the first group account.

Further still, notifications may be sent to other non-shared devices (e.g., personal devices), assigned to user accounts associated with the sender's group account. For instance, a group account may be generally linked to a shared device, and the group account may include one or more user accounts. Each user account may correspond to an individual that is also associated with the group account. In some embodiments, personal devices (e.g., devices associated with a particular individual's user account), may also be provided with a notification each time a message, or more generally a communication, is sent by that group account. For instance, if the first individual, having a user account that is also included by the first group account, also has a personal device, then in response to the message being sent to the second individual, a notification may also be sent to the first individual's personal device that indicates that a new message has been sent from their associated group account. If, in some embodiments, speaker identification processing is able to identify the first individual as being the speaker, then the first individual's personal device may not receive a notification, however other personal devices associated with other user accounts also included by the first group account may still receive such a notification.

In some embodiments, an individual may send a message to a group account associated with a shared electronic device using that shared electronic device. For example, an individual may say an utterance, "Alexa, send a message to my home's group account: 'Please pick up some milk'." In response to determining that the wakeword (e.g., "Alexa") was uttered, the shared electronic device may send audio data representing the utterance to a speech-processing system. The speech-processing system may determine, using speaker identification processing, that a speaker of the utterance corresponds to a first user having a first user account. Furthermore, the speech-processing system may also determine that the shared electronic device is associated with a first group account with which the first user account is a member of. For instance, the first group account may be associated with a plurality of user accounts, where each user account corresponds to a user of the shared electronic device. In one exemplary embodiment, the first group account may be associated with at least two or three user accounts. In response to determining that a recipient of the message is the group account, as well as determining that a sender of the message corresponds to a first user of a first user account associated with the group account, the message may be stored for the group account, as well as any other user account associated with the group account. In some embodiments, the message may be stored as an unread message by the group account and each of the user accounts except for the first user account, as the first user corresponds to a sender of the message. The first user account may have the message stored, however the message may be marked as having been read.

In some embodiments, a notification may be generated and sent to the shared electronic device, where the notification causes an indicator of the shared electronic device to indicate that a new message has been received for the group account. For example, one or more lights of the shared electronic device may be caused to illuminate in a particular manner that indicate that a message has been received, and in particular, that a message has been received for a group account that the device is associated with. Furthermore, in one embodiment, notifications may be generated and sent to various personal devices associated with members (e.g., user accounts) associated with the group account, except for the user account associated with the sender.

In some embodiments, a shared device, such as the shared devices described above, may correspond to sound controlled electronic device. One type of sound controlled electronic device may be a voice activated electronic device. In particular, a voice activated electronic device may correspond to one type of sound controlled electronic device that is capable of being activated in response to a wakeword being uttered. In response to determining that a wakeword has been uttered, the voice activated electronic device may, in some embodiments, send the audio data representing a spoken utterance subsequently following the wakeword to a speech-processing system for processing and analyzing the audio data. The speech-processing system may then generate and send a response to the voice activated electronic device, as well as, or alternatively, communicate with one or more additional systems for obtaining content to be rendered by the voice activated electronic device, and/or may cause one or more additional electronic devices to output content and/or perform a particular action (e.g., turn on a light, preheat an oven, etc.). Additionally, the voice activated electronic device may store one or more wakewords within its local memory. If a determination is made that audio data received from the audio input devices (e.g., microphones)

matches the wakeword, the voice activated electronic device may begin sending audio data representing some or all of the audio captured by the voice activated electronic device to the speech-processing system.

Spoken voice commands, in some embodiments, may be prefaced by a wakeword, which may also be referred to as a trigger expression, wake expression, or activation word. In response to detecting the wakeword being uttered, a voice activated electronic device may be configured to detect and interpret any words that subsequently follow the detected wakeword as actionable inputs or commands. In some embodiments, the voice activated electronic device may be activated by a phrase or grouping of words, which the voice activated device may also be configured to detect. The voice activated device, therefore, may also be able to detect and interpret any words subsequently following that phrase or grouping of words.

As used herein, the term "wakeword" may correspond to a "keyword" or "key phrase," an "activation word" or "activation words," or a "trigger," "trigger word," or "trigger expression." One exemplary wakeword may be a name, such as the name, "Alexa," however persons of ordinary skill in the art will recognize that the any word (e.g., "Amazon"), or series of words (e.g., "Wake Up" or "Hello, Alexa") may alternatively be used as the wakeword. Furthermore, the wakeword may be set or programmed by an individual operating a voice activated electronic device, and in some embodiments more than one wakeword (e.g., two or more different wakewords) may be available to activate a voice activated electronic device. In yet another embodiment, the trigger that is used to activate a voice activated device may be any series of temporally related sounds.

As used herein, the term "utterance" may correspond to a spoken word, statement, or sound. In some embodiments, an utterance may include the wakeword followed by an invocation, such as a request, question, or command. In this particular instance, the utterance may begin with the wakeword being spoken, and may end when a last word, phoneme, or sound is spoken. For example, an utterance may correspond to the question, "Alexa—What is the weather currently like?" As another example, an utterance may be, "Alexa—Play my workout music." Further still, an utterance, which need not include the wakeword, may be, "Turn up the volume" or "Call mom."

Another type of sound controlled electronic device may be a sound activated electronic device. Such sound activated electronic device may function similarly to voice activated electronic devices, except that, for sound activated electronic devices, the trigger may be a non-verbal sound. For example, the sound of a door opening, an alarm going off, glass breaking, a telephone ringing, or any other sound may alternatively be used to activate a sound controlled electronic device. In this particular scenario, detection of a non-verbal sound may occur in a substantially similar manner as that of a verbal wakeword for a voice activated electronic device. For example, the sound of a door opening, when detected, may activate a sound activated electronic device, which in turn may activate a burglar alarm.

In some embodiments, the sound controlled electronic device may also correspond to a manually activated electronic device. A manually activated electronic device, as described herein, may correspond to a device that is capable of being activated in response to a manual input from an individual (e.g., pressing a button, touching a portion of a touch screen, performing an action on a device). For example, a tap-to-talk device is one type of manually activated device. Such tap-to-talk devices, for instance, are capable of obtaining and outputting audio data in response to a button being pressed by an individual. In some embodiments, a sound controlled electronic device (e.g., a voice activated electronic device and/or a sound activated electronic device) may include manual activated functionality such that an individual may interact with the device using voice (e.g., speech prefaced by a wakeword), sound (e.g., a particular trigger sound), and/or a manual input (e.g., a button press, a touch of a screen, etc.). However, in some embodiments, an electronic device may be configured to include a single activation functionality (e.g., only voice activated, or only manually activated).

FIG. 1 is an illustrative diagram of an exemplary system for sending a message from one shared electronic device to another shared electronic device, in accordance with various embodiments. In a non-limiting, exemplary embodiment, a first individual 2 may send a first message to a second individual 12 using a first shared electronic device 100*a*. For instance, individual 2 may speak utterance 4, "Alexa—Send a message to John: 'Want to have dinner at my place?'," where individual 2 intends for some or all of utterance 4 to be sent to one or more devices associated with a particular contact (e.g., a contact having the name "John"). In some embodiments, individual 2 may speak utterance 4 in the vicinity of first shared electronic device 100*a*. First shared electronic device 100*a*, in one embodiment, may correspond to a voice activated electronic device, capable of causing one or more actions to occur in response to being activated. For example, in response to determining that a wakeword (e.g., "Alexa") was uttered, first shared electronic device 100*a* may begin sending audio data representing utterance 4 to computing system 200 to be processed, and to cause one or more actions to occur (e.g., generate a response message, receive content, send data to one or more additional devices, etc.).

In some embodiments, computing system 200 may include speech recognition processing that may be capable of determining an intent of utterance 4. For example, upon receipt of the audio data representing utterance 4, text data representing the audio data may be generated, and an intent of utterance 4 may be determined using the generated text data. In the illustrative embodiment, the intent of utterance 4 may be for audio of a message—"Want to have dinner at my place?—to be sent to a contact having a name "John." Computing system 200 may determine that a portion of utterance 4 matched a sample utterance framework, "{Wakeword}—Send a {Communication Type} to {Contact Name}: {Message}," and extract values for these terms. As an illustrative example, the term {Contact Name} may be mapped to the name "John." Computing system 200 may determine a user account associated with first shared electronic device 100*a*, and determine a contact listed within the user account having the name "John" in order to determine a target recipient of the message.

In some embodiments, upon successfully processing the audio data representing utterance 4 such that an action (e.g., sending a message to another individual's electronic device) is to be performed, computing system 200 may generate a confirmation message, and may send that confirmation message to first shared electronic device 100*a*. For example, computing system 200 may generate audio data representing response 6, "Ok," which may be sent from computing system 200 to first shared electronic device 100*a*. Response 6 may then be output by first shared electronic device 100*a* such that individual 2 will be aware that their request has been successfully processed, and the intended action is to occur. In some embodiments, if the intent is unable to be determined, or if additional information is needed to perform the requested action, then computing system 200 may generate and send a follow-up message to electronic device 100*a* in order to facilitate the request. For example, if there are two or more contacts named "John" associated with the user account associated with individual 2, then computing system 200 may inquire as to which contact individual 2 intends to have the message sent to.

First shared electronic device 100*a*, in one embodiment, corresponds to a shared voice activated electronic device. Any individual may be capable of interacting with first shared electronic device 100*a* by speaking its wakeword (e.g., "Alexa"). Furthermore, first shared electronic device 100*a* may be located within an individual's residence, office, or any suitable area, such that it may be interacted with by one or more individuals. For example, first shared electronic device 100*a* may be located in a living room of a house, and any family member of the household may speak an utterance prefaced by a wakeword of first shared electronic device 100*a*. In response, first shared electronic device 100*a* may communicate with computing system 200 to cause one or more actions to occur.

In some embodiments, computing system 200 may employ speaker identification processing to determine who the speaker of utterance 4 is. For example, upon receipt of the audio data representing utterance 4, computing system 200 may determine that the voice that spoke utterance 4 substantially matches voice biometric data associated with a user account corresponding to individual 2. Persons of ordinary skill in the art will recognize, however, that in some embodiments, speaker identification processing may be performed locally by first shared electronic device 100*a*, and the aforementioned is merely exemplary. By determining that individual 2 spoke utterance 4, computing system 200 may be able to identify the intended target of the message of utterance 4 by searching through a contact list associated with a user account of individual 2. Additionally, by determining that individual 2 spoke utterance 4, the message may be indicated as having been sent from individual 2, as opposed to be listed as being received from a first group account associated with first shared electronic device 100*a*.

After determining that a message is to be sent to second individual 12, and determining that second individual 12 is associated with second shared electronic device 100*b*, computing system 200 may send the audio data representing the message portion of utterance 4 (e.g., "Want to have dinner at my place?") to second shared electronic device 100*b*. However, in some embodiments, the audio data representing the message portion may be stored within a message data store on computing system 200. In this particular scenario, the audio data may be obtained and sent to the recipient's device (e.g., second shared electronic device 100*b*) upon computing system 200 receiving a request to do so.

Additionally, computing system 200 may include one or more communications systems that may generate an introductory message to be used with the message portion of utterance 4. For example, an introductory message may indicate a number of messages that have been received (e.g., new messages and/or old messages), as well as a sender, or senders, that those messages were received from. As an illustrative example, in response to the message being sent from first shared electronic device 100*a*, an introductory message may be generated indicating that one message has been received, and that message was received from the first group account associated with first shared electronic device 100*a*.

In some embodiments, an individual may receive the messages (e.g., listen, read, view, etc.) using their electronic device. For example, second individual 12 may speak an utterance 14 to second shared electronic device 100*b* to obtain any messages sent to their second group account and/or their particular account associated with their user account. For instance, utterance 14 may be, "Alexa, do I have any messages?" In response to determining that a wakeword (e.g., "Alexa") for second shared electronic device 100*b* has been uttered, second shared electronic device 100*b* may begin sending audio data representing utterance 14 to computing system 200 to determine an intent of utterance 14. For instance, computing system 200 may determine that the intent of utterance 14 is to output any messages for a second group account associated with second shared electronic device 100*b* and/or for a user account associated with individual 12. In one embodiment, one or more indicators (e.g., lights, graphical user interfaces, etc.) may be used by second shared electronic device 100*b* to indicate to individual 12 that a message has been received.

Upon receiving the audio data representing utterance 14, one or more communications systems of computing system 200 may generate second audio data representing a response 16 to be output, where response 16 includes an introductory message and the message uttered by individual 2. The introductory message may be crafted such that it indicates to the individual consuming the message: (i) how many messages have been received, and (ii) who the message(s) was (were) received from. Additional information, such as urgency of the message, time or receipt, and the like, may also be indicated by the introductory message. As an illustrative example, the introductory message may be "You have received one message from the Jones Household: 'Want to have dinner at my place?'" This may allow individual 12 to know that they have received one message, and that the message was received from first shared electronic device 100*a*.

In some embodiments, computing system 200, and in particular one or more communications systems and/or systems associated with the communication system(s), may perform exemplary process 150. Process 150 may, in a non-limiting embodiment, begin at step 152. At step 152, first audio data may be received from a first device. For instance, audio data representing utterance 4 may be received by computing system 200 from first shared electronic device 100*a*. In some embodiments, in addition to receiving the first audio data, a first device identifier associated with the first device may also be received. For instance, a first device identifier for first shared electronic device 100*a* may be received by computing system 200 at a substantially same time as the first audio data. The device identifier may allow computing system 200 to identify a group account registered for computing system 200 that is assigned to first shared electronic device 100*a*. In some embodiments, the group account may indicate a household, office, or residency, associated with the first device.

At step 154, speaker identification processing may be performed to the first audio data. Speaker identification processing, which is described in greater detail below with reference to FIG. 2, attempts to determine "who" spoke, as opposed to attempting to determine "what" was said. Using a device identifier associated with the first device, a group account associated with the first device may be determined, and voice biometric data associated with one or more user accounts included by the group account may be accessed. The first audio data may be analyzed to determine a voice print (e.g., frequency spectrum, cadence, accent, meter, etc.)

of the utterance (e.g., utterance 4), which may then be compared with the various voice biometric data stored for the group account associated with the first device. Upon performing the speaker identification, process 150 may proceed to step 156, where a determination may be made as to whether or not the speaker of the utterance represented by the first audio data is recognized. For instance, at step 156, a determination is made as to whether or not a voice print of the utterance matches voice biometric data associated with a member (e.g., a user account) of the group account.

If, at step 156, the speaker is not able to be determined, then process 150 may proceed to step 158. At step 158, the group account assigned to the first device may be determined. In one embodiment, a device identifier received for the first device may be used to determine an entry in a communications table stored by computing system 200 that indicates a relationship of certain group accounts and device identifiers. For instance, the first device's device identifier may correspond to an entry in a communications table, where that entry also indicates a group account identifier that is associated with that device identifier. For instance, the group account identifier may identify a corresponding a name and/or identity of the group account assigned to the first device. As an illustrative example, first shared electronic device 100a may have a first device identifier (e.g., 111.xxx), which is sent to computing system 200 substantially with the audio data. Computing system 200 may access a communications table stored thereon to determine an entry to the communications table that the first device identifier corresponds to. After determining the entry, a group account identifier (e.g., 111.yyy) may be determined for that particular entry. Using the group account identifier, a first group account, such as the "Jones Household," may be determined. Messages sent from first shared electronic device 100a may, in the illustrative embodiment, be indicated as having been sent by the first group account. For instance, if a particular speaker identifier is unable to be determined using speaker identification processing, or if a speaker identifier is determined to not match voice biometric data associated with one or more user accounts, then that message may be sent from the group account of that shared electronic device.

At step 160, a recipient group account may be determined. The recipient group account may correspond to a group account associated with an intended recipient of the message included within the spoken utterance. For example, utterance 4 may indicate that a message, "Want to have dinner at my place?", is to be sent to a contact "John." In one embodiment, the first audio data representing the utterance may be provided to a speech-processing system, which may employ speech recognition and natural language understanding functionality to the first audio data to determine an intent of the utterance. For example, the speech-processing system may determine that utterance 4 includes a message, and may also determine an intended recipient of that message. A list of contacts associated with the first group account may be accessed to determine which contact that is associated with that identified recipient, and a recipient group account and/or user account for that contact may be determined. After determining the recipient's group account, a group account identifier for the group account may be obtained, which may enable computing system 200 to determine a device identifier for a second device that the recipient's group account is assigned to. As an illustrative example, the first group account may include a listing of contacts associated therewith. Upon determining the intended recipient of the message is a contact having the name "John," the listing of contacts may be parsed to determine if any contacts included therein correspond to that recipient. If so, a group account associated with that contact may be determined, and a group account identifier for that group account may be determined (e.g., 222.yyy). Using the group account identifier, a device identifier (e.g., 222.xxx) associated with the group account may be determined.

At step 162, message metadata for a message included within the spoken utterance may be generated, where the message metadata may indicate that a message was received from the first group account, and that the message is intended to be sent to a recipient. The message metadata may, for instance, include information indicating who the message was sent by, a time that the message was received, and/or an importance of that message, amongst other details. In some embodiments, an introductory message may be generated by computing system 200 in response to a request to output messages for that particular group account and/or user account, where the introductory message is generated using the information included by the message metadata.

In some embodiments, in addition to, or instead of, generating the message metadata, an introductory message may be generated, where the introductory message may be used to inform the recipient of the message's receipt, as well as who the message was received from. The introductory message may be used to indicate a number of messages that have been received, as well as a sender associated with each of the messages (e.g., one message from "Mom," two messages from "Home."). As an illustrative example, introductory message from response 16 may be generated that indicates that the message's sender was a group account associated with a shared device. For example, the group identifier that was determined for first shared electronic device 100a may have corresponded to the "Jones Household," and therefore the generated introductory message may indicate that the sender of the message is the "Jones Household." In some embodiments, a sample introductory message stored by computing system 200 may take the form of "You received {Number of Messages Received} message(s) from {Group Identifier}." Therefore, using this example, the introductory message may be "You received one message from the Jones Household," where {Number of Messages Received}: One; and {Group Identifier}: the Jones Household. However, persons of ordinary skill in the art will recognize that the introductory message may not be generated until a request to play messages is received, and the aforementioned is merely exemplary.

At step 164, the message and the message metadata may be stored by computing system 200. For example, the message and message metadata may be stored in a message data store of computing system 200, where the message and message metadata may be linked to both the sender's group account and the recipient's group account. In this way, upon the recipient group account receiving a request to output messages received for that group account, the message, as well as an introductory message for that message, may be generated by computing system 200 and sent to the corresponding device that the group account of the recipient is assigned to.

In some embodiments, computing system 200 may generate second audio data representing the message and the introductory message, which may be sent to a second device associated with the recipient's device identifier. For example, audio data representing the introductory message and the message (e.g., "You received one message from the Jones Household: 'Want to have dinner at my place?'") may be sent from one or more communications systems of computing system 200 to second shared electronic device 100b. For instance, the determined recipient identifier may indicate that the intended recipient is associated with a second group account, corresponding to a second device identifier of second shared electronic device 100b.

In some embodiments, a notification may be generated and sent to each member of the first group account and the second group account. The notification may indicate that a new communication has been sent and received, respectively. For example, in response to storing the message for the second group account and any user account associated with the second group account, each user account may be sent the notification. In particular, personal devices associated with each user account may be sent the notification such that the user associated with those devices are aware of the newly received communication. Similarly, user accounts associated with the first group account may also be sent a notification indicating that the communication was sent to the second group account. For example, in response to storing the message for the first group account, and each user account associated with the first group account, a notification may be generated and sent to any personal devices associated with the user accounts so that the users associated with those devices are aware that a new message was sent by the group account.

If, however, at step 156, a speaker is recognized by the speaker identification processing performed to the first audio data, then process 150 may proceed to step 166. For instance, if the speaker identification processing determines that a speaker identifier of the audio data representing utterance 4 substantially matches a speaker identifier corresponding to a particular user account of the first device's assigned group account, then utterance 4 may be said to have been spoken by the individual associated with that user account (e.g., individual 2). At step 166, a user account corresponding to the identified speaker may be determined. In some embodiments, as similarly described above with reference to step 158, a device identifier corresponding to the first device may be received by computing system 200. Using the device identifier, a group account assigned to the first device may be determined. Upon determining the speaker identifier of the first audio data, a user account associated with that group account may be determined. As an illustrative example, a first group account may be assigned to first shared electronic device 100a. The first group account may include one or more user accounts, each associated with different individuals that commonly interact with first shared electronic device 100a. For instance, individual 2 may have a user account on computing system 200 that is associated with the first group account. In response to determining that the speaker of the first audio data corresponds to the voice biometric data for individual 2, computing system 200 may determine that the sender of the message (e.g., "Want to have dinner at my place?") is individual 2, and therefore that the message that was uttered is to be sent as from the user account of individual 2, as opposed to being sent from the first group account assigned to first shared electronic device 100a.

At step 168, a recipient group account may be determined. Steps 168 and 160, in one embodiment, may be substantially similar to each other, and the previous description may apply. At step 170, message metadata indicating that a message was sent from the user account may be generated. For example, the speaker identification processing may determine that individual 2 spoke utterance 4. Therefore, the message metadata may be generated such that an introductory message may be generated by computing system 200 such that introductory message indicates that the message was sent from individual 2. As an illustrative example, in response to receiving audio data representing utterance 14, individual 12 may be provided with a different message indicating that individual 2 sent the message "Want to have dinner at my place?" For instance, the introductory message, in this particular scenario, may be "You received one message from Paul: 'Want to have dinner at my place?'" At step 172, the message to be sent to the recipient, as well as the message metadata for that message, may be stored by computing system 200, such as using a message data store of computing system 200. In some embodiments, step 172 and step 164 may be substantially similar to one another, and the previous description may apply.

In some embodiments, a notification may be generated and sent to each member of the first group account and the second group account, except for the user account associated with the identified speaker. For example, in response to storing the message for the first group account, and each user account associated with the first group account except for the user account associated with the identified speaker, a notification may be generated and sent to any personal devices associated with the user accounts so that the users associated with those devices are aware that a new message was sent by the group account. The user account associated with the identified speaker, in one embodiment, may have the message that was sent marked as "read." In this way, computing system 200 may be capable of intelligently marking the message as not new for the user account of the identifier speaker such that that individual does not receive a notification indicating that the message that he/she just sent has been received. The message may automatically be marked as not new.

Figure 2:
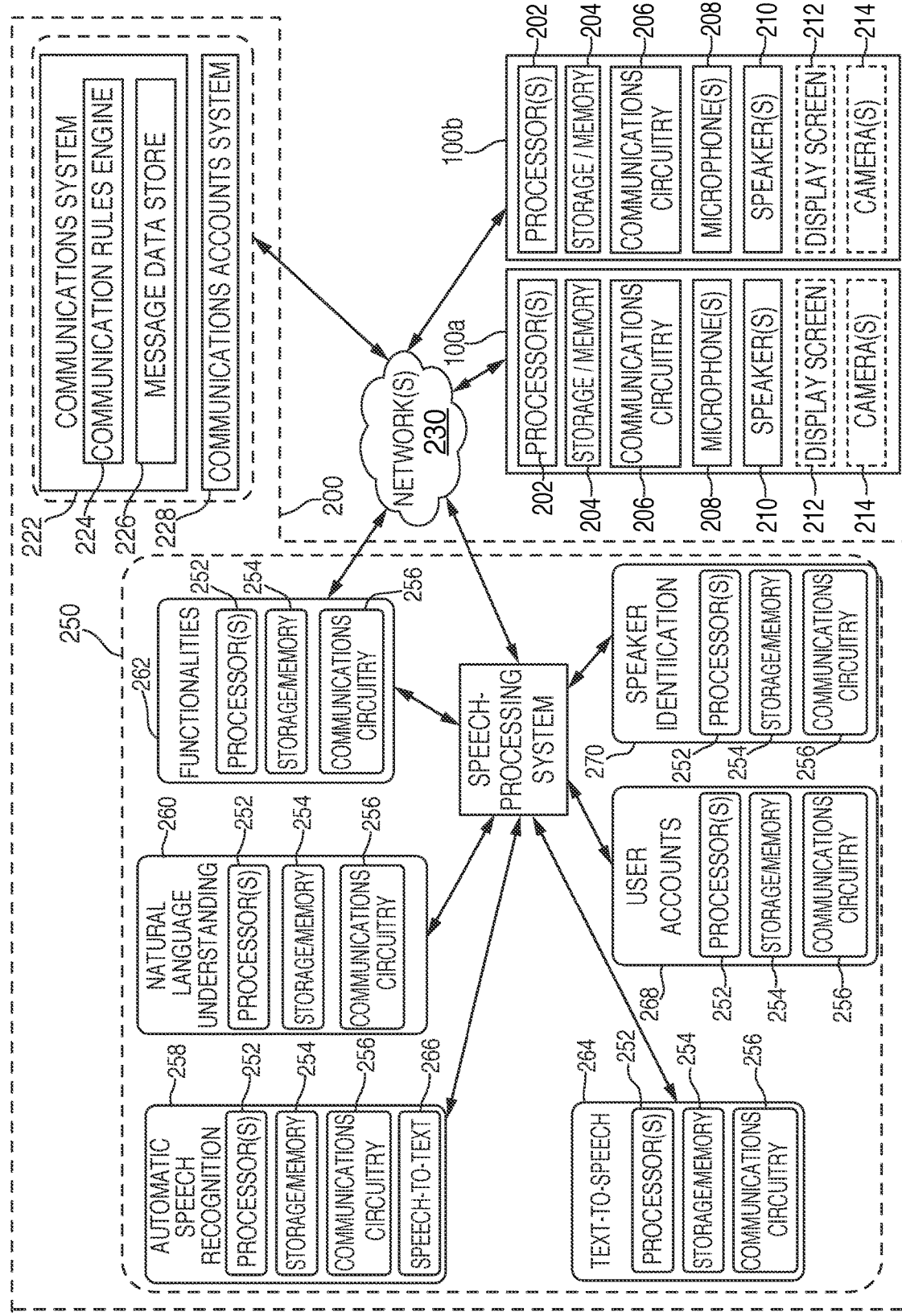
FIG. 2 is an illustrative diagram of the exemplary system architecture of FIG. 1, in accordance with various embodiments.

FIG. 2 is an illustrative diagram of the exemplary system architecture of FIG. 1, in accordance with various embodiments. Shared electronic devices 100a and 100b (collectively "shared electronic device(s) 100" or "electronic device(s) 100") may, in some embodiments, include sound controlled functionality, such as one or more voice or sound activated components. In some embodiments, electronic device 100 may be configured to communicate with computing system 200, and in particular a speech-processing system 250, in response to detecting an utterance including a wakeword, which may subsequently be followed by a request/question/statement. Similarly, electronic device 100 may alternatively or additionally include one or more manually activated components for manually activation functionality. In this particular scenario, electronic device 100 may also be configured, in one embodiment, to communicate with computing system 200, and thus speech-processing system 250, in response to a manual input being detected by one or more input mechanisms, such as a touch screen, a button, and/or a switch, for example.

In a non-limiting embodiment, electronic device 100 may be capable of being activated in response to detecting a specific sound, such as a wakeword, as well as, or alternatively, via one or more inputs. After detecting a specific sound (e.g., a wakeword or trigger expression), electronic device 100 may recognize commands (e.g., audible commands, inputs) within captured audio, and may perform one or more actions in response to the received commands. Furthermore, electronic device 100 may also be configured to perform one or more actions in response to detecting a particular touch, or mechanical, input(s) via electronic device 100.

Electronic device 100 may correspond to any suitable type of electronic device including, but are not limited to, desktop computers, mobile computers (e.g., laptops, ultrabooks), mobile phones, smart phones, tablets, televisions, set top boxes, smart televisions, personal display devices, large scale display devices (e.g., billboards, street signs, etc.), personal digital assistants ("PDAs"), gaming consoles and/or devices, smart furniture, smart household devices (e.g., refrigerators, microwaves, etc.), smart vehicles (e.g., cars, trucks, motorcycles, etc.), smart transportation devices (e.g., ships, trains, airplanes, etc.), wearable devices (e.g., watches, pins/broaches, headphones, etc.), and/or smart accessories (e.g., light bulbs, light switches, electrical switches, etc.). In some embodiments, electronic device 100 may be relatively simple or basic in structure such that no, or a minimal number of, mechanical input option(s) (e.g., keyboard, mouse, track pad) or touch input(s) (e.g., touch screen, buttons) are included. For example, electronic device 100 may be able to receive and output audio, and may include power, processing capabilities, storage/memory capabilities, and communication capabilities. However, in other embodiments, electronic device 100 may include one or more components for receiving mechanical inputs or touch inputs, such as a touch screen and/or one or more buttons.

Electronic device 100, in one embodiment, may include a minimal number of input mechanisms (e.g., a power on/off switch) such that functionality of electronic device 100 may solely or primarily be through audio input and audio output. For example, electronic device 100 may include, or be in communication with, one or more microphones that listen for a wakeword by continually monitoring local audio. In response to the wakeword being detected, electronic device 100 may establish a connection with computing system 200 and/or speech-processing system 250, send audio data to computing system 200 and/or speech-processing system 250, and await/receive a response from computing system 200 and/or speech-processing system 250. In some embodiments, however, non-voice/sound activated devices may also communicate with computing system 200 and/or speech-processing system 250 (e.g., push-to-talk devices). For example, in response to a button or touch screen being pressed, or a button or touch screen being pressed and held, a microphone associated with electronic device 100 may begin recording local audio, establish a connection with computing system 200 and/or speech-processing system 250, send audio data representing the captured audio to computing system 200 and/or speech-processing system 250, and await/receive a response, and/or action to be occur, from computing system 200 and/or speech-processing system 250.

Persons of ordinary skill in the art will recognize that although in the illustrative embodiment computing system 200 includes speech-processing system 250, this is merely exemplary, and speech-processing system 250 may be separate from computing system 200. For example, speech-processing system 250 may be located within a dedicated computing device or computing system, which may or may not be in communication with computing system 200 and/or one or more additional devices.

Electronic device 100 may include one or more processors 202, storage/memory 204, communications circuitry 206, one or more microphones 208 or other audio input devices (e.g., transducers), one or more speakers 210 or other audio output devices, a display screen 212, and one or more cameras 214 or other image capturing components. However, one or more additional components may be included within electronic device 100, and/or one or more components may be omitted. For example, electronic device 100 may also include a power supply or a bus connector. As still yet another example, electronic device 100 may include one or more additional input and/or output mechanisms, such as one or more buttons, or one or more switches or knobs. Furthermore, while electronic device 100 may include multiple instances of one or more components, for simplicity only one of each component has been shown.

In some embodiments, electronic device 100 may correspond to a manually activated device, or may include the functionality of a manually activated device. A manually activated device, as described herein, may correspond to a device that is capable of being activated in response to a manual input (e.g., pressing a button, touching a portion of a touch screen, performing an action on a device). For example, a tap-to-talk device is one type of manually activated device. Such tap-to-talk devices, for instance, are capable of obtaining and outputting audio data in response to a button being pressed.

In one embodiment, electronic device 100 may be in communication with an additional processing device including one or more of: processor(s) 202, storage/memory 204, communications circuitry 206, microphone(s) 208, speaker(s) 210, display screen 212, and/or camera(s) 214. For example, a centralized control device of electronic device 100 may include one or more microphone(s) 208. These microphone(s) 208 may receive audio input signals, which in turn may be sent to computing system 200 and/or speech-processing system 250 in response to a wakeword engine of electronic device 100 determining that a wakeword was uttered.

Processor(s) 202 may include any suitable processing circuitry capable of controlling operations and functionality of electronic device 100, as well as facilitating communications between various components within electronic device 100. In some embodiments, processor(s) 202 may include a central processing unit ("CPU"), a graphic processing unit ("GPU"), one or more microprocessors, a digital signal processor, or any other type of processor, or any combination thereof. In some embodiments, the functionality of processor(s) 202 may be performed by one or more hardware logic components including, but not limited to, field-programmable gate arrays ("FPGA"), application specific integrated circuits ("ASICs"), application-specific standard products ("ASSPs"), system-on-chip systems ("SOCs"), and/or complex programmable logic devices ("CPLDs"). Furthermore, each of processor(s) 202 may include its own local memory, which may store program systems, program data, and/or one or more operating systems. However, processor(s) 202 may run an operating system ("OS") for electronic device 100, and/or one or more firmware applications, media applications, and/or applications resident thereon. In some embodiments, processor(s) 202 may run a local client script for reading and rendering content received from one or more websites. For example, processor(s) 202 may run a local JavaScript client for rendering HTML or XHTML content received from a particular URL accessed by electronic device 100.

Storage/memory 204 may include one or more types of storage mediums such as any volatile or non-volatile memory, or any removable or non-removable memory implemented in any suitable manner to store data for electronic device 100. For example, information may be stored using computer-readable instructions, data structures, and/or program systems. Various types of storage/memory may include, but are not limited to, hard drives, solid state drives, flash memory, permanent memory (e.g., ROM), electronically erasable programmable read-only memory ("EE- PROM"), CD-ROM, digital versatile disk ("DVD") or other optical storage medium, magnetic cassettes, magnetic tape, magnetic disk storage or other magnetic storage devices, RAID storage systems, or any other storage type, or any combination thereof. Furthermore, storage/memory 204 may be implemented as computer-readable storage media ("CRSM"), which may be any available physical media accessible by processor(s) 202 to execute one or more instructions stored within storage/memory 204. In some embodiments, one or more applications (e.g., gaming, music, video, calendars, lists, etc.) may be run by processor(s) 202, and may be stored in memory 204.

In some embodiments, storage/memory 204 may include a media system, which may be configured to facilitate communications between electronic devices 100 and computing system 200. For example, the media system may store one or more communications protocols that may be executed by processor(s) 202 for facilitating communications for device 100. In some embodiments, a sessions initiation protocol ("SIP") may be used to facilitate media transfer between electronic device 100 and one or more of computing system 200 and another electronic device 100. SIP, for example, is an application layer protocol that is text based, and may employ Real-time Transport Protocol ("RTP") or Secure Real-time Transport Protocol ("SRTP") functions. In particular, PJSIP communications functionality may be employed to support audio, video, presence, and messaging communications for electronic device 100. In some embodiments, a Web Real-Time Communications ("WebRTC") protocols may be employed by electronic device 100. In a non-limiting embodiment, the media system may include instructions that indicate which communications protocols to employ for facilitating media transfer between devices based on a device type of electronic device 100. For example, if electronic device 100 does not include display 212 and/or camera 214, then the media system may indicate that PJSIP should be used, whereas if electronic device 100 includes display 212 and/or camera 214 then the media system may indicate that WebRTC protocols should be used.

In some embodiments, storage/memory 204 may include one or more systems and/or databases, such as a speech recognition system, a wakeword database, a sound profile database, and a wakeword detection system. The speech recognition system may, for example, include an automatic speech recognition ("ASR") component that recognizes human speech in detected audio. The speech recognition system may also include a natural language understanding ("NLU") component that determines user intent based on the detected audio. Also included within the speech recognition system may be a text-to-speech ("TTS") component capable of converting text to speech to be outputted by speaker(s) 210, and/or a speech-to-text ("STT") component capable of converting received audio signals into text to be sent to computing system 200 and/or speech-processing system 250 for processing.

The wakeword database may be a database stored locally by storage/memory 204 of electronic device 100, and may include a list of a current wakeword for electronic device 100, as well as one or more previously used, or alternative, wakewords for voice activated electronic device. In some embodiments, an individual may set or program a wakeword for their electronic device 100. The wakeword may be programmed directly on electronic device 100, or a wakeword or wakewords may be set by the individual via a local client application that is in communication with computing system 200 and/or speech-processing system 250. For example, an individual may use their mobile device having the speech-processing system application running thereon to set the wakeword. The specific wakeword may then be communicated from the mobile device to speech-processing system 250, which in turn may send/notify electronic device 100 of the individual's selection for the wakeword. The selected activation may then be stored in the wakeword database of storage/memory 204. In some embodiments, additional trigger expressions or permutations of the wakeword may also be stored within storage/memory 204. For example, specific trigger expressions or words that indicate the presence of the wakeword may also be stored within storage/memory 204. In some embodiments, audio watermarks, indicating a specific action or message, may also be stored within storage/memory 204.

In some embodiments, sound profiles for different words, phrases, commands, or audio compositions are also capable of being stored within storage/memory 204, such as within a sound profile database. For example, a sound profile of audio may be stored within the sound profile database of storage/memory 204 on electronic device 100. In this way, if a particular sound (e.g., a wakeword or phrase) is detected, a corresponding command or request may be ignored, for example. A sound profile, for example, may correspond to a frequency and temporal decomposition of a particular audio file or audio portion of any media file, such as an audio fingerprint or spectral representation.

The wakeword detection system may include an expression detector that analyzes an audio signal produced by microphone(s) 208 to detect a wakeword, which generally may be a predefined word, phrase, or any other sound, or any series of temporally related sounds. Such an expression detector may be implemented using keyword spotting technology, as an example. A keyword spotter is a functional component or algorithm that evaluates an audio signal to detect the presence of a predefined word or expression within the audio signal detected by microphone(s) 208. Rather than producing a transcription of words of the speech, a keyword spotter generates a true/false output (e.g., a logical I/O) to indicate whether or not the predefined word or expression was represented in the audio signal. In some embodiments, an expression detector may be configured to analyze the audio signal to produce a score indicating a likelihood that the wakeword is represented within the audio signal detected by microphone(s) 208. The expression detector may then compare that score to a wakeword threshold to determine whether the wakeword will be declared as having been spoken.

In some embodiments, a keyword spotter may use simplified ASR techniques. For example, an expression detector may use a Hidden Markov Model ("HMM") recognizer that performs acoustic modeling of the audio signal and compares the HMM model of the audio signal to one or more reference HMM models that have been created by training for specific trigger expressions. An HMM model represents a word as a series of states. Generally, a portion of an audio signal is analyzed by comparing its HMM model to an HMM model of the trigger expression, yielding a feature score that represents the similarity of the audio signal model to the trigger expression model.

In practice, an HMM recognizer may produce multiple feature scores, corresponding to different features of the HMM models. An expression detector may use a support vector machine ("SVM") classifier that receives the one or more feature scores produced by the HMM recognizer. The SVM classifier produces a confidence score indicating the likelihood that an audio signal contains the trigger expression. The confidence score is compared to a confidence threshold to make a final decision regarding whether a particular portion of the audio signal represents an utterance of the trigger expression (e.g., wakeword). Upon declaring that the audio signal represents an utterance of the trigger expression, electronic device 100 may then begin transmitting the audio signal to speech-processing system 250 for detecting and responds to subsequent utterances made by an individual.

In some embodiments, storage/memory 204 may store voice biometric data associated with one or more individuals. For example, an individual that operates electronic device 100 may have a registered user account on computing system 200 (e.g., within accounts system 268). In some embodiments, electronic device 100 may be associated with a group account, and various individuals may have user accounts that are operating under the rules and configurations of the group account. As an illustrative example, first shared electronic device 100a may be associated with a first group account on computing system 200, the first group account being for a family that lives at a household where first shared electronic device is located. Each family member may also have a user account that is linked to the first group account (e.g., a parent, a child, etc.), and therefore each user account may obtain some or all of the rights of the first group account. For example, electronic device 100 may have a first group account on computing system 200 registered to a particular family or group, and each of the parents and children of the family may have their own user account registered under the parent's registered account. In one illustrative embodiment, voice biometric data for each individual may be stored by that individual's corresponding user account. The voice biometric data, for instance, may correspond to a "voice print" or "voice model" of a particular individual, which may be a graphical representation of a person's voice including a frequency decomposition of that individual's voice.

Upon receiving audio data representing an utterance, such as utterance 4 of FIG. 1, a voice print of that audio data may be generated using speaker identification functionality stored within storage/memory 204. The voice print of the utterance may indicate the different frequency components of the spoken words over time as the utterance was spoken. The generated voice print may then be compared to a previously generated voice print, which may be referred to as a reference voice print, specific to a particular individual's speech. A difference between the generated voice print and the reference voice print may be determined and, if the difference is less than or equal to a predefined threshold value, then the two voice prints may be declared as corresponding to a same individual's voice indicating that that individual spoke the utterance. If the difference is larger than the predefined threshold value, then the generated voice print may be said to be unassociated with the individual's voice, and therefore may indicate that the individual did not speak the utterance. In some embodiments, the speaker identification functionality may compare any generated voice print to one or more reference voice prints in order to try and find a match. Therefore, for each individual's user account associated with a group account, voice biometric data (e.g., acoustic features) for that particular individual may be included. This may allow electronic device 100 to attempt and identify a speaker of a particular utterance locally. However, persons of ordinary skill in the art will recognize that electronic device 100 may not perform speaker identification processing, and alternatively speaker identification processing may be performed by computing system 200 (e.g., speaker identification system 270), or no speaker identification processing may be performed all together.

Communications circuitry 206 may include any circuitry allowing or enabling one or more components of electronic device 100 to communicate with one another, one or more additional devices, servers, and/or systems. For example, communications circuitry 206 may facilitate communications between electronic device 100 and computing system 200. As an illustrative example, audio data representing an utterance (e.g., utterance 4 of FIG. 1) may be transmitted over a network 230, such as the Internet, to computing system 200 using any number of communications protocols. For example, network(s) 230 may be accessed using Transfer Control Protocol and Internet Protocol ("TCP/IP") (e.g., any of the protocols used in each of the TCP/IP layers), Hypertext Transfer Protocol ("HTTP"), WebRTC, SIP, and wireless application protocol ("WAP"), are some of the various types of protocols that may be used to facilitate communications between electronic device 100 and computing system 200. In some embodiments, electronic device 100 and computing system 200 and/or one or more additional devices or systems (e.g., speech-processing system 250) may communicate with one another via a web browser using HTTP. Various additional communication protocols may be used to facilitate communications between electronic device 100 and computing system 200, including, but not limited to, Wi-Fi (e.g., 802.11 protocol), Bluetooth, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS-136/TDMA, iDen, LTE or any other suitable cellular network protocol), infrared, BitTorrent, FTP, RTP, RTSP, SSH, and/or VOIP.

Communications circuitry 206 may use any communications protocol, such as any of the previously mentioned exemplary communications protocols. In some embodiments, electronic device 100 may include an antenna to facilitate wireless communications with a network using various wireless technologies (e.g., Wi-Fi, Bluetooth, radiofrequency, etc.). In yet another embodiment, electronic device 100 may include one or more universal serial bus ("USB") ports, one or more Ethernet or broadband ports, and/or any other type of hardwire access port so that communications circuitry 206 allows electronic device 100 to communicate with one or more communications networks.

Electronic device 100 may also include one or more microphones 208 and/or transducers. Furthermore, one or more microphones located within a separate device may be in communication with electronic device 100 to capture sounds for electronic device 100. Microphone(s) 208 may be any suitable component capable of detecting audio signals. For example, microphone(s) 208 may include one or more sensors for generating electrical signals and circuitry capable of processing the generated electrical signals. In some embodiments, microphone(s) 208 may include multiple microphones capable of detecting various frequency levels. As an illustrative example, electronic device 100 may include multiple microphones (e.g., four, seven, ten, etc.) placed at various positions about electronic device 100 to monitor/capture any audio outputted in the environment where electronic device 100 is located. The various microphones 208 may include some microphones optimized for distant sounds, while some microphones may be optimized for sounds occurring within a close range of electronic device 100. In some embodiments, microphone(s) 208 may only begin to detect audio signals in response to a manual input to electronic device 100. For example, a manually activated device may begin to capture audio data using microphone(s) 208 in response to a user input, such as pressing a button, tapping a touch screen, or providing any touch input gesture to a touch input component.

Electronic device 100 may include one or more speakers 210. Furthermore, electronic device 100 may be in communication with one or more speaker(s) 210. Speaker(s) 210 may correspond to any suitable mechanism for outputting audio signals. For example, speaker(s) 210 may include one or more speaker units, speaker housings, transducers, arrays of speakers, and/or arrays of transducers that may be capable of broadcasting audio signals and or audio content to a surrounding area where electronic device 100 may be located. In some embodiments, speaker(s) 210 may include headphones or ear buds, which may be wirelessly wired, or hard-wired, to electronic device 100, that may be capable of broadcasting audio directly to an individual.

In some embodiments, one or more microphones 208 may serve as input devices to receive audio inputs. Electronic device 100, in the previously mentioned embodiment, may then also include one or more speakers 210 to output audible responses. In this manner, electronic device 100 may function solely through speech or audio, without the use or need for any input mechanisms or displays, however this is merely exemplary.

Display screen 212 may correspond to a display device and/or touch screen, which may be any size and/or shape and may be located at any portion of electronic device 100. Various types of displays may include, but are not limited to, liquid crystal displays ("LCD"), monochrome displays, color graphics adapter ("CGA") displays, enhanced graphics adapter ("EGA") displays, variable graphics array ("VGA") display, or any other type of display, or any combination thereof. Still further, a touch screen may, in some embodiments, correspond to a display device including capacitive sensing panels capable of recognizing touch inputs thereon. For instance, display screen 212 may correspond to a projected capacitive touch ("PCT"), screen include one or more row traces and/or driving line traces, as well as one or more column traces and/or sensing lines. In some embodiments, display screen 212 may be an optional component for electronic device 100. For instance, electronic device 100 may not include display screen 212. Such devices, sometimes referred to as "headless" devices, may output audio, or may be in communication with a display device for outputting viewable content.

Display screen 212, in one non-limiting embodiment, may include an insulator portion, such as glass, coated with a transparent conductor, such as indium tin oxide ("InSnO" or "ITO"). In general, one side of the touch screen display may be coated with a conductive material. A voltage may be applied to the conductive material portion generating a uniform electric field. When a conductive object, such as a human finger, stylus, or any other conductive medium, contacts the non-conductive side, typically an outer surface of display screen 212, a capacitance between the object and the conductive material may be formed. Processor(s) 202 may be capable of determining a location of the touch screen associated with where the capacitance change is detected, and may register a touch input as occurring at that location.

In some embodiments, display screen 212 may include multiple layers, such as a top coating layer, a driving line layer, a sensing layer, and a glass substrate layer. As mentioned previously, the glass substrate layer may correspond to an insulator portion, while the top coating layer may be coated with one or more conductive materials. The driving line layer may include a number of driving lines, and the sensing layer may include a number of sensing lines, which are described in greater detail below. Persons of ordinary skill in the art will recognize that one or more additional layers, or spaces between layers, may be included. Furthermore, persons of ordinary skill in the art will recognize that any number of driving lines and sensing lines for driving the line layer and the sensing layer, respectively, may be used.

In some embodiments, the driving lines and the sensing lines of the driving line layer and the sensing line layer, respectively, may form a number of intersection points, where each intersection functions as its own capacitor. Each sensing line may be coupled to a source, such that a charge is provided to each sensing line, and changes in capacitance of a particular driving line and sensing line are detectable thereby. In response to a conductive object being brought proximate, or substantially touching an outer surface of the top coating layer, a mutual capacitance of a particular capacitor (e.g., an intersection point) may reduce in magnitude. In other words, a voltage drop may be detected at a location on display screen 212 corresponding to where a conductive object contacted display screen 212.

A change in capacitance may be measured to determine a location on the touch screen where the object has contacted the surface. For example, if an individual touches a point on display screen 212, then a corresponding driving line and sensing line that intersect at that point may be identified. A location of the point may have one or more pixels associated with that location, and therefore one or more actions may be registered for an item or items that are displayed at that location. Processor(s) 202 of electronic device 100 may be configured to determine which pixels are associated with a particular location point, and which item or items are also displayed at that pixel location. Furthermore, electronic device 100 may be configured to cause one or more additional actions to occur to the item or items being displayed on display screen 212 based on a temporal duration the touch input, and or if one or more additional touch inputs are detected. For example, an object that contacted display screen 212 at a first location may be determined, at a later point in time, to contact display screen 212 at a second location. In the illustrative example, an object may have initially contacted display screen 212 at the first location and moved along a particular driving line to the second location. In this scenario, a same driving line may have detected a change in capacitance between the two locations, corresponding to two separate sensing lines.

The number of driving lines and sensing lines, and therefore the number of intersection points, may directly correlate to a "resolution" of a touch screen. For instance, the greater the number of intersection points (e.g., a greater number of driving lines and sensing lines), the greater precision of the touch input. For instance, a touch screen display screen 212 having 100 driving lines and 100 sensing lines may have 100 intersection points, and therefore 100 individual capacitors, while a touch screen display screen 212 having 10 driving lines and 10 sensing lines may only have 10 intersection points, and therefore 10 individual capacitors. Therefore, a resolution of the touch screen having 100 intersection points may be greater than a resolution of the touch screen having 10 intersection points. In other words, the touch screen having 100 intersection points may be able to resolve a location of an object touching the touch screen with greater precision than the touch screen having 10 intersection points. However, because the driving lines and sensing lines require a voltage to be applied to them, this may also mean that there is a larger amount of power drawn by electronic device 100, and therefore the fewer driving lines and/or sensing lines used, the smaller the amount of power that is needed to operate the touch screen display.

In some embodiments, display screen 212 may correspond to a high-definition ("HD") display. For example, display screen 212 may display images and/or videos of 720p, 1080p, 1080i, or any other image resolution. In these particular scenarios, display screen 212 may include a pixel array configured to display images of one or more resolutions. For instance, a 720p display may present a 1024 by 768, 1280 by 720, or 1366 by 768 image having 786,432; 921,600; or 1,049,088 pixels, respectively. Furthermore, a 1080p or 1080i display may present a 1920 pixel by 1080 pixel image having 2,073,600 pixels. However, persons of ordinary skill in the art will recognize that the aforementioned display ratios and pixel numbers are merely exemplary, and any suitable display resolution or pixel number may be employed for display screen 212, such as non-HD displays, 4K displays, and/or ultra displays.

In some embodiments, electronic device 100 may include one or more cameras 214, corresponding to any suitable image capturing component or components capable of capturing one or more images and/or videos. Camera(s) 214 may, in some embodiments, be configured to capture photographs, sequences of photographs, rapid shots (e.g., multiple photographs captured sequentially during a relatively small temporal duration), videos, or any other type of image, or any combination thereof. In some embodiments, electronic device 100 may include multiple cameras 214, such as one or more front-facing cameras and/or one or more rear facing cameras. Furthermore, camera(s) 214 may be configured to recognize far-field imagery (e.g., objects located at a large distance away from electronic device 100) or near-filed imagery (e.g., objected located at a relatively small distance from electronic device 100). In some embodiments, the camera(s) may be high-definition ("HD") cameras, capable of obtaining images and/or videos at a substantially large resolution (e.g., 726p, 1080p, 1080i, etc.). In some embodiments, camera(s) 214 may be optional for electronic device 100. For instance, camera(s) 214 may be external to, and in communication with, electronic device 100. For example, an external camera may be capable of capturing images and/or video, which may then be provided to electronic device 100 for viewing and/or processing.

Persons of ordinary skill in the art will recognize that, in some embodiments, display screen 212 and/or camera(s) 214 may be optional for electronic device 100. For instance, electronic device 100 may function using audio inputs and outputting audio, and therefore display screen 212 and/or camera(s) 214 may not be included. Furthermore, in some embodiments, electronic device 100 may not include display screen 212 and/or camera(s) 214, but instead may be in communication with display screen 212 and/or camera(s) 214. For example, electronic device 100 may be connected to a display screen via a Wi-Fi (e.g., 802.11 protocol) connection such that visual content sent to electronic device 100 may be sent to the display screen, and output thereby.

In one exemplary embodiment, electronic device 100 may include an additional input/output ("I/") interface. For example, electronic device 100 may include one or more input components capable of receiving user inputs. Various types of input components may include, but are not limited to, keyboards, buttons, switches, a mouse, joysticks, or an external controller may be used as an input mechanism for the I/O interface. In some embodiments, the output portion of the I/O interface of electronic device 100 may include one or more lights, light emitting diodes ("LEDs"), or other visual indicator(s). Persons of ordinary skill in the art will recognize that, in some embodiments, one or more features of the output portion of the I/O interface may be included in a purely voice activated version of electronic device 100. For example, one or more LED lights may be included on electronic device 100 such that, when microphone(s) 208 receive audio, the one or more LED lights become illuminated signifying that audio has been received by electronic device 100. In some embodiments, one or more vibrating mechanisms or other haptic features may be included with electronic device 100 to provide a haptic response to an individual.

In some embodiments, electronic device 100 may include radio-frequency identification ("RFID") functionality and/or near field communication ("NFC") functionality. Furthermore, in some embodiments, electronic device 100 may include one or more infrared ("IR") sensors and one or more IR emitters. The IR sensors/emitters may be used to determine depth information. For example, in one embodiment, a distance of an individual from electronic device 100 may be determined using the one or more IR sensors/emitters. Depth determination may be performed using any depth determination technique. In some embodiments, a distance between an individual and electronic device 100 may be employed as a basis for presenting content with varying density using display screen 212. For example, when an individual is at a distance A from electronic device 100, electronic device 100 may display weather data for a current day. However as the user moves closer to electronic device 100, such as at a distance B from electronic device 100, which may be less than distance A, electronic device 100 may display weather data for a current week. For instance, as the individual gets closer to electronic device 100, the ability of the individual to see denser content increases, and as the individual moves father away from electronic device 100, the individual's ability to see denser content decreases. This, for example, may ensure that the content displayed by electronic device 100 is continually relevant and readable by the individual.

Computing system 200, in a non-limiting, exemplary embodiment, may include speech-processing system 250. However, in other embodiments, speech-processing system 250 may be separate from, or in communication with, computing system 200. Generally, speech-processing system 250 may, in some embodiments, include one or more remote devices capable of receiving and sending content from/to one or more electronic device, such as electronic device 100. Speech-processing system 250 may include various components and systems including, but not limited to, automatic speech recognition ("ASR") system 258, natural language understanding ("NLU") system 260, functionalities system 262, text-to-speech ("TTS") system 264, accounts system 268, and speaker identification system 270. In some embodiments, speech-processing system 250 may also include computer readable media, including, but not limited to, flash memory, random access memory ("RAM"), and/or read-only memory ("ROM"). Speech-processing system 250 may also include various systems that store software, hardware, logic, instructions, and/or commands for speech-processing system 250, or any other system, or any combination thereof.

ASR system 258 may be configured to recognize human speech in detected audio, such as audio captured by microphone(s) 208, which may then be transmitted to speech-processing system 250. ASR system 258 may include, in one embodiment, one or more processor(s) 252, storage/memory 254, and communications circuitry 256. Processor(s) 252, storage/memory 254, and communications circuitry 256 may, in some embodiments, be substantially similar to processor(s) 202, storage/memory 204, and communications circuitry 206, which are described in greater detail above, and the aforementioned descriptions may apply. In some embodiments, ASR system 258 may include speech-to-text ("STT") system 266. STT system 266 may employ various speech-to-text techniques. However, techniques for transcribing speech into text are well known in the art and need not be described in further detail herein, and any suitable computer implemented speech to text technique may be used to convert the received audio signal(s) into text, such as SOFTSOUND speech processing technologies available from the Autonomy Corporation, which is headquartered in Cambridge, England, United Kingdom.

ASR system 258 may include an expression detector that analyzes audio signals received by speech-processing system 250, such as the expression detector mentioned above with regards to electronic device 100. Such an expression detector may be implemented using keyword spotting technology, as an example. A keyword spotter is a functional component or algorithm that evaluates an audio signal to detect the presence of a predefined word or expression, such as a passphrase or other sound data, within the audio signals. Rather than producing a transcription of words of the speech, a keyword spotter generates a true/false output (e.g., a logical I/O) to indicate whether or not the predefined word or expression was represented in the audio signal. In some embodiments, an expression detector may be configured to analyze the audio signal to produce a score indicating a likelihood that the wakeword or phrase, is represented within the audio signal. The expression detector may then compare that score to a threshold value to determine whether the wakeword or phrase will be declared as having been spoken.

NLU system 260 may be configured such that it determines user intent based on the received audio data. For example, NLU system 260 may determine that the intent of utterance 4 is for initiating a communications session with a device, associated with a particular name (e.g., initiate a communications session with "John"). In response to determining the intent of the utterance, NLU system 260 may communicate the received command to an appropriate subject matter server or skill on functionalities system 262 to perform one or more tasks, and/or retrieve an appropriate response or response information. NLU system 260 may include processor(s) 252, storage/memory 254, and communications circuitry 256 which, in one embodiment, may be substantially similar to processor(s) 202, storage/memory 204, and communications circuitry 206 of electronic device 100, and the previous description may apply.

Functionalities system 262 may, for example, correspond to various action specific systems or servers, sometimes referred to as "skills," capable of processing various task specific actions. Functionalities system 262 may further correspond to first party applications and/or third party applications capable of performing various tasks or actions. For example, based on the context of the audio received from electronic device 100, speech-processing system 250 may use a certain functionality to generate a response, or to obtain response information, which in turn may be communicated back to electronic device 100. For instance, an utterance may ask for weather information, and therefore functionalities system 262 may access a weather application to obtain current weather information for a location associated with electronic device 100. Functionalities system 262 may also include processor(s) 252, storage/memory 254, and communications circuitry 256. In some embodiments, one or more skills of functionalities system 262 may be in communication with communications system 222 via network 230. For example, a communications functionality may be accessed which causes speech-processing system 250 to send certain data (e.g., audio data, text data, speaker identifiers, etc.) to communications system 222.

TTS system 264 may employ various text-to-speech techniques. However, techniques for transcribing speech into text are well known in the art and need not be described in further detail herein, any suitable computer implemented speech to text technique may be used to convert the received audio signal(s) into text, such as SOFTSOUND speech processing technologies available from the Autonomy Corporation, which is headquartered in Cambridge, England, United Kingdom. TTS system 264 may also include processor(s) 252, storage/memory 254, and communications circuitry 256.

Accounts system 268 may store one or more user accounts corresponding to users having a registered account on computing system 200. For example, a parent may have a registered account on computing system 200, and each of the parent's children may have their own user account registered under the parent's registered account. In some embodiments, accounts system 268 may store acoustic features, such as voice biometric information, for a specific user account. This may allow speaker identification techniques to be used to match a voice to voice biometric data associated with a specific user account. In some embodiments, accounts system 268 may store a telephone number assigned to a particular user account, a device identifier associated with a particular device, a communications identifier associated with a particular user account and/or group account, or any other suitable information, or any combination thereof.

Speaker identification system 270, in some embodiments, may correspond to any suitable device/system capable of identifying a particular person's voice from an audio signal. Speaker identification system 270 may determine whether a current voice being used to speak matches known voice biometric data associated with a particular individual's voice. In some embodiments, voice biometric data may be stored within accounts system 268 for various individuals having a user account stored thereby. For example, individual 2 may have a user account on computing system 200 (e.g., stored within accounts system 268), which may be associated with electronic device 100a. Stored within the user account may be voice biometric data associated with a voice of individual 2. Therefore, when an utterance, such as utterance 4, is detected by electronic device 100a, and subsequently when audio data representing that utterance is received by computing system 200, speaker identification system 270 may determine whether the voice used to speak utterance 4 matches, to at least a predefined confidence threshold, the stored voice biometric information associated with individual 2 stored by their user account. If so, then this may indicate that individual 2 is the likely speaker of utterance 4.

In some embodiments, speaker identification system 270 may receive audio data representing an utterance, or a copy of the audio data, at a substantially same time as ASR system 258. The audio data may be divided into audio frames representing time intervals, with which a number of values or features representing qualities of the audio data may be determined, along with a set of those values (e.g., feature vectors or audio feature vectors) representing features/qualities of the audio data for each audio frame. For example, each audio frame may include 25 ms of audio, and the frames may start at 10 ms intervals. This may result in a sliding window where adjacent audio frames include 15 ms of overlapping audio. Persons of ordinary skill in the art will recognize that many different acoustic features may be determined, and each feature may be representative of a particular quality of the audio data. Some exemplary approaches that may be used to process the received audio data may include, but art not limited to, mel-frequency cepstral coefficients ("MFCCs"), perceptual linear predictive ("PLP") techniques, neural network feature vector techniques, linear discriminant analysis, and semi-tied covariance matrices. Speaker identification system 270 may also include a scoring component that determines respective confidence scores indicating how likely it is that an input utterance was spoken by a particular user.

When audio data is received by computing system 200, ASR system 258, speaker identification system 270, and/or any other suitable component of speech-processing system 250, may performing windowing functions to the audio data to generate framed audio data. The size of each audio frame may depend on a particular configuration of speech-processing system 250, and persons of ordinary skill in the art will recognize that any audio frame size may be used. For example, as mentioned previously, each audio frame may include 25 milliseconds of audio data, and may overlap with 10 milliseconds of a next audio frame, resulting in a sliding window. Performing a windowing function may include multiplying a time record by a finite-length window with an amplitude that varies smoothly and gradually toward zero at its edges. By performing windowing, endpoints of the waveforms of respective audio frames of audio data meet, resulting in a continuous waveform without sharp transitions. A fast Fourier transform ("FFT") may be performed to convert the waveforms in each audio frame of the framed audio data from its original domain (e.g., time) to a representation in a frequency domain (thereby creating frequency domain framed audio data). Audio processing techniques other than or in addition to FFT may be used to transform audio data (e.g., waveforms) into data that can be processed as needed.

In some embodiments, user recognition feature extraction may be performed on the frequency domain framed audio data. User recognition feature extraction may include performing frame level feature extraction and/or utterance level feature extraction. The frame level feature extraction may determine which frame of a universal background model ("UBM") the frame corresponds to. The UBM may be a Gaussian mixture model, a deep neural network, etc. The utterance level feature extraction may analyze aligned speech frames to derive feature vectors of fixed length (i.e., the user recognition feature/vector data). The feature extraction may continue until voice activity is no longer detected in the input audio data, at which point an endpoint of the speech may be identified and speech processing may end. Feature extraction may, in some embodiments, be performed on all the audio data received from the electronic device 100. Alternatively, feature extraction may only be performed on audio data including speech. Feature extraction and user recognition feature extraction may include determining values (i.e., features) representing qualities of the frequency domain framed audio data, along with quantitating those features into values (i.e., acoustic feature vectors or audio feature vectors). Feature extraction may determine automatic speech recognition feature/vector data, which may assist with speech recognition processing for ASR system 258, and user recognition feature extraction may determine user recognition feature/vector data, which may assist with speaker identification/user recognition for speaker identification system 270. The feature/vector data and the user recognition feature/vector data may include the same features/vectors, different features/vectors, or may include some overlapping features/vectors. A number of approaches may be used to extract features/vectors from the frequency domain framed audio data, such as MFCCs, PLP techniques, neural network feature vector techniques, linear discriminant analysis, semi-tied covariance matrices, and persons of ordinary skill in the art will recognize that any other suitable approach may be employed.

Speaker identification system 270 may perform speaker identification using various data including user recognition features/vector data, and training data that may correspond to sample audio data corresponding to known users associated with a particular device (e.g., electronic device 100). Speaker identification system 270 may generate confidence scores indicating a likelihood that a particular utterance was spoken by one of the users associated with a particular device, and may determine whether any of these confidence scores is greater than a predefined confidence score threshold. If so, then that may indicate a likelihood that a certain user is the speaker of the utterance. If two or more confidence scores are determined to be in excess of the confidence score threshold, then speaker identification system 270 may select the user having the greater confidence score, or may prompt the device to obtain additional information to resolve the speaker's identity.

In some embodiment, training data may be obtained and stored by user accounts system 268. The training data may be stored as waveforms and/or corresponding features/vectors, and may correspond to data from various audio samples, each audio sample associated with a known user and/or user identity. For example, each user known to the system may be associated with some set of training data for the known user. Speaker identification system 270 may then use the training data to compare against incoming audio data (represented by user recognition feature/vector data) to determine an identity of a user speaking an utterance. The training data may be associated with multiple users of multiple devices and therefore may be associated with both a user that spoke the respective utterance, as well as electronic device 100, which provided the audio data representing the spoken utterance.

The training data for a particular user may include a feature vector of the same size as a vector of the user recognition feature/vector data. Thus, for example, if a feature vector is of size F, the training data may also be a feature vector of size F. To create such a training data feature vector, during a training period computing system 200 may either prompt a user to speak sample audio data or may identify sample audio data known to have been spoken by a particular user. The system may then process the sample audio data to create sample training data (e.g., a feature vector of size F). The training data may then be stored by user accounts system 268 and saved for use during runtime user verification processing.

Persons of ordinary skill in the art will recognize that although each of ASR system 258, NLU system 260, subject matter/skills system 262, TTS system 264, accounts system 268, and speaker identification system 270 may each include instances of processor(s) 252, storage/memory 254, and communications circuitry 256, and those instances of processor(s) 252, storage/memory 254, and communications circuitry 256 within each of ASR system 258, NLU system 260, functionalities system 262, TTS system 264, and accounts system 268 may differ. For example, the structure, functionality, and style of processor(s) 252 within ASR system 258 may be substantially similar to the structure, functionality, and style of processor(s) 252 within NLU system 260, however the actual processor(s) 252 need not be the same entity.

Computing system 200 may also include, in a non-limiting embodiment, a communications system 222, which may be configured to facilitate communications between two or more electronic devices. For example, communications system 222 may be capable of facilitating a communications session between electronic device 100*a* and at least electronic device 100*b*. Upon speech-processing system 250 determining that an intent of an utterance is for a communications session to be established with another device, computing device 200 may access communications system 222 to facilitate the communications session between the initiating device and the receiving device. For example, communications system 222 may employ VoIP functionality to facilitate audio, video, and/or text data communications between the initiating device and the recipient device.

As an illustrative example, a communications session between two devices is described below to illustrate how the communications session may be established. In one example embodiment, an individual (e.g., individual 2) may speak an utterance (e.g., "Alexa, send a message to John: 'Want to have dinner at my place?'") to their electronic device (e.g., electronic device 100*a*). In response to detecting the device's wakeword (e.g., "Alexa"), the electronic device may begin sending audio data representing the utterance to computing system 200, and in particular speech-processing system 250. Upon receipt, ASR system 250 may perform speech recognition processing, such as speech-to-text processing, to the audio data to generate text data representing the audio data. The text data may then be passed to NLU system 260 to determine an intent of the utterance. For example, NLU system 260 may include a listing of sample utterances to be used to disambiguate the spoken words and determine an action intended to occur for the utterance. In some embodiments, a messaging speechlet system may be included within NLU system 260 that includes one or more sample utterance frameworks. If the format of the spoken utterance substantially matches one of these sample utterances, then that may indicate that an intent of the utterance was for a communications session to be initiated. For instance, one example sample utterance may be "{Wakeword}, send a message to {Contact Name}: {Message}." If the spoken utterance's text data substantially matches this sample utterance's framework, then NLU system 260 may determine that the intent of the utterance was to start a communications session with a contact of the user, and may also determine that the intended target of the communications session is "John" (e.g., {Contact Name}: John). After determining that a message is to be sent to a contact named "John," communications system 222 may access communications accounts system 228 to determine a device identifier (e.g., a device address) associated with the contact, "John."

In some embodiments, communications system 222 may establish a communications session between an initiating device and a recipient device using one or more VoIP protocols including, but not limited to SIP, RTP, RTCP, SRTP, and SDP. In one illustrative embodiment, a SIP signaling command may be provided to communications system 222 for communicating with the recipient device. In particular, PJSIP functionality adds a new "user-to-user" header that indicates the device pair for the communications session.

In one embodiment, communications system 222 may include a communication rules engine 224. Communications rules engine may store various rules for how certain communications between group accounts and user accounts are to behave. For example, communications rules engine 224 may store communications routing information and instructions for how different messages may be sent from one device to another device depending on a variety of parameters including, but not limited to, if the sender device is a shared device, if the recipient device is a shared device, if the sender device is a personal device, if the recipient device is a personal device, if there are any personal and/or shared devices associated with the sender device and/or recipient device, and/or whether or not speaker identification was able to positively identify a speaker. In one illustrative embodiment, communication rules engine 224 may store a communications table indicating various device identifiers, group account identifiers, communication identifiers, and device types for various devices interacting with communications system 222, as described in greater detail below with reference to FIG. 3.

In some embodiments, communications system 222 may also include a message data store 226. Message data store 226, in a non-limiting embodiment, may correspond to any suitable type of storage/memory, such as that of storage/memory 204, 254, capable of storing one or more messages sent/received. For example, when an individual sends a message (e.g., "Want to have dinner at my place?") from their shared electronic device to another shared electronic device, that message may be stored by communications system 222 using message data store 226. In some embodiments, message data store 226 may be structured to store audio data representing audio message, video data representing video messages, image data representing image messages, text data representing text messages, and/or message notification metadata. When an individual utters a request to receive messages received for their user account and/or group account, communications system 222 may access message data store 226 to obtain those messages, and may send the appropriate message data (e.g., audio, video, image, text, etc.) to the corresponding requesting device (e.g., personal device, shared device). In some embodiments, message data store 226 may store each message with a corresponding communications identifier, group account identifier, user account identifier, and/or device identifier with which that message is directed to. For example, if a first individual sends an audio message to a second individual, audio data representing that audio message may be stored by message data store 226 with a group account identifier associated with the second individual's corresponding group account, as stored by communications accounts system 228. This way, when an individual requests to receive messages associated with their group account, message data store 226 may be accessed to obtain any messages currently stored thereby that are associated with that group account's group account identifier.

Communications rules engine 224 may employ several communications rules for messages sent/received to/from one or more participants. First, a device type of the sending device may be determined. For example, a determination may be made as to whether or not a device identifier associated with the device that the audio data representing utterance 4, which include a message to be sent to another individual's device, is associated with a shared device. Next, a determination may be made by speaker identification system 270 as to whether or not a speaker that spoke the utterance was able to be identified. Using these two parameters, for instance, communications rules engine 224 may be configured to cause communications system 222 to facilitate communications between two or more devices.

Communications accounts system 228 may also store one or more group accounts corresponding to one or more shared devices. For example, a shared device, such as shared electronic device 100, may have its own group account stored on communications accounts system 228. The group account may be associated with the shared device, and may also be linked to one or more individual's user accounts. For example, shared electronic device 100 may be associated with a first group account corresponding to a first grouping of individual (e.g., a family). One or more user accounts may also be associated with the first group account (e.g., individual members of the family), corresponding to individuals that may be capable of interacting with shared electronic device 100. Information, settings, and/or preferences, for example, for each user account may be stored within a user account database. In some embodiments, communications accounts system 228 and accounts system 268 may communicate with one another via network 230 to provide one another with account information associated with certain devices and communications accounts. For example, user accounts system 268 may store voice biometric data for a particular user account, which may then be provided to communications accounts system 228 to determine a communications identifier and/or other communications information associated with that user account so as to allow a device associated with the user account to communicate with one or more additional devices.

FIG. 3 is an illustrative diagram of an exemplary communications table, in accordance with various embodiments. Communications table 300, in a non-limiting embodiment, includes entries 302-314. Each entry may indicate a device identifier, a group account identifier, a communication identifier, and a device type associated with a communication that is received or a communication to be sent. In some embodiments, each instance of a communication that is intended to be sent from one device to another device may result in an new entry added to communications table 300. However, persons of ordinary skill in the art will recognize that upon receiving a communication from a device, additional entries may not be required, and the entry associated with a device's particular device identifier may be stored for any suitable amount of time by communications system 222.

Device identifiers, as illustrated by communications table 300, may correspond to any suitable identification means for a device that may interact with communications system 222. Various types of device identifiers may include, but are not limited to, media access control ("MAC") identifiers, serial numbers, internet protocol ("IP") addresses, global positioning addresses, telephone numbers, messaging identifiers, and the like. As an illustrative example, when first shared electronic device 100a of FIG. 1 sends audio data representing utterance 4 to computing system 200, that audio data may be received with a device identifier unique to first shared electronic device 100a (e.g., device identifier of row 302: "111.xxx"). Each device identifier, in one embodiment, is unique to that particular device with which it is associated with. Therefore, no two device identifiers should be identical, however persons of ordinary skill in the art will recognize that it is possible for two device identifiers to be the same.

A group account identifier may correspond to an identifier that indicates a particular group account on computing system 200, which may be stored by communications accounts system 228, that a corresponding device identifier is associated with. For example, as seen by entry 302, a device may have a device identifier 111.xxx, which may be associated with a group account identifier 111.yyy. The group account identifier may include multiple device identifiers, indicating that each corresponding device associated with one of those device identifiers is part of a same group account. For example, entry 304 may correspond to a device identifier 222.xxx, but may also correspond to the group account identifier 111.yyy. This may indicate that a first device corresponding to entry 302 and a second device corresponding to entry 304 are both associated with a same group account (e.g., group account identifier 111.yyy). Similarly, entry 306 may also indicate that another device, having device identifier 333.xxx, is also associated with the same group account as the first and second devices associated with entries 302 and 304. Further still, entries 308, 310, and 312 may also be associated with a same group account, corresponding to group account identifier 111.bbb, which differs from group account identifier 111.yyy.

In some embodiments, each device identifier may also have an associated communication identifier. A communications identifier may be any suitable type of identifier used for identifying a participant of a communication. As an illustrative example, entry 302 may indicate that a first device associated with device identifier 111.xxx has a communications identifier 111.zzz. In some embodiments, the communications identifier may be configurable by a user of an associated device. For example, the communications identifier may be any suitable alphanumeric string of numbers, letters, and/or characters, that allow an individual to identify themselves when they send a message to, or receive a message from, another individual.

Also stored by communications table 300 may be a device type associated with each device entry into table 300. For example, communications table 300 may indicate whether a device corresponding to a particular device identifier is a shared device or a mobile device. In one embodiment, a mobile device may be considered to be a personal device in that it is typically associated with a particular individual.

When audio data representing an utterance is received, a device identifier may also be received, either with the audio data (e.g., part of a header of the audio data), or separately (e.g., metadata received in addition to the audio data). Upon receiving the device identifier, communications system 222 may determine an entry within communications table 300 matching that device identifier. After determining the device identifier, a corresponding group identifier for that device identifier may also be determined, and a determination of whether or not that device is a shared device may occur.

FIGS. 4A-D are illustrative flowcharts of an exemplary process for sending a message from a first device to a second device, in accordance with various embodiments. Process 400, in a non-limiting embodiment, may begin at step 402. At step 402, first audio data representing a first message may be received from a first device. For example, individual 2 may speak utterance 4 to first shared electronic device 100a. Upon determining that a wakeword (e.g., "Alexa") for first shared electronic device 100a was uttered, first shared electronic device 100a may begin sending audio data representing utterance 4 to communications system 200, and in particular to speech-processing system 250. Persons of ordinary skill in the art will recognize that any type of communication may be received with the intention of being sent to another device, and the use of audio data representing a message is merely exemplary. For example, an audio communication (e.g., telephone call) or a video communication (e.g., video call) may be received from a first device.

At step 404, first text data representing the first audio data may be generated. For instance, upon receipt, speech-processing system 250 may provide the first audio data to ASR system 258, which may include STT system 266 for performing automatic speech recognition processing to the first audio data, which may generate first text data representing the first audio data. At step 406, a first intent of the first message may be determined. For instance, ASR system 258 may provide the first text data to NLU system 260, which attempts to determine an intent of an utterance using natural language understanding processing. In the illustrative embodiment, the intent that is determined may be that the first utterance includes a message to be sent to a first contact. For example, NLU system 260 may compare the first text data with one or more sample utterances to try and extract slot values for varies slots of a sample utterance. For instance, if the utterance is "Alexa, send a message to John: 'Want to have dinner at my place?'," then NLU system 260 may determine that the format of the text data substantially matches a sample utterance of the format "{Wakeword}, send a message to {Contact Name}: {Message}." Using this framework, the slot values {Contact Name} and {Message} may be extracted as being {John} and {Want to have dinner at my place?}, respectively. In the illustrative embodiment, the contact name may be used to determine an intended target recipient for the message to be sent. For example, upon determining that a target recipient corresponds to a contact having the name {Contact Name}, communications system 222 may access communications accounts system 228 to determine contact information associated with that contact.

At step 408, a first device identifier associated with the first device may be received. In some embodiments, the first device identifier may be a MAC address, a serial number, or any other unique identifier associated with the first device. At step 410, a first group account associated with the first device identifier may be determined. For example, upon receiving the first device identifier, communications system 222 may access communications table 300 to determine a group identifier that is associated with the received first device identifier. For instance, if the first device identifier received corresponds to entry 302 (e.g., device identifier 111.xxx), then the group account identifier associated therewith would correspond to group account identifier 111.yyy. At step 412, a second group account associated with the first contact may be determined. For instance, upon determining the first group account associated with the first device identifier, a listing of contacts associated each user account associated with the first group account may be obtained, and a determination of a group account matching that contact name may occur. As an illustrative example, the first device may have a first device identifier corresponding to a first group account. That first group account may include a listing of contacts associated with any user accounts of that group account, as well as the group account itself. For instance, the listing of contacts for the group account may be formed from a first listing of contacts associated with a first user account associated with the first group account and a second listing of contacts associated with a second user account associated with the group account.

At step 414, a determination may be made of a shared device associated with the second group account. For example, if the second group account corresponds to the group account identifier 111.bbb, then communications system 222 may receive the device identifiers of entries 308, 310, and 312 (e.g., 111.aaa, 222.aaa, 333.aaa). After receiving the device identifiers associated with the determined group account identifier, communications system 222 may determine, using communications table 300, which, if any, of the received device identifiers are associated with a shared device. As an illustrative example, communications table 300 may indicate that a second device, having device identifier 111.aaa, associated with the second group account identifier 111.bbb, may be a shared device, and therefore communications system 222 may return device identifier 111.aaa as a second shared device associated with the identified second group account for the first contact.

At step 416, a determination may be made as to whether there are any user accounts associated with the second group account. For instance, communications system 222 may poll communications table 300 to determine any user accounts corresponding to the second group account's identifier. Upon obtaining the user accounts, communications system 222 may determine which, if any, of those user accounts have a non-shared devices (e.g., personal devices) associated with them. As an illustrative example, if the second group account is associated with a first user account, a second user account, and a third user account, then device identifiers corresponding to non-shared devices associated with those user accounts may be obtained. If, at step 416, it is determined that there are user accounts associated with the second group account, then process 400 may proceed to step 418. At step 418, device identifiers associated with user account(s) may be determined. For example, if the second group account has one user account associated with it, then a device identifier associated with one or more personal devices of the user account may be determined. Persons of ordinary skill in the art will recognize that a user account may be associated with two or more group accounts, and therefore two or more shared devices, and the aforementioned is merely illustrative. Process 400 may then proceed from step 418 to step 420. However, if at step 416, it is determined that there are no user accounts associated with the second group account, then process 400 may proceed to step 420.

At step 420, a determination may be made as to whether or not the first device is a shared device. For instance, based on the received device identifier, communications system 222 may determine whether or not the device type of that particular entry for communications table 300 corresponds to a shared device or a personal device. For example, entry 302 may correspond to a shared device. If, at step 420, it is determined that the first device is not a shared device, then process 400 may proceed to step 426 of FIG. 4B. However, if at step 420, it is determined that the first device is a shared device, then process 400 may proceed to step 422. Persons of ordinary skill in the art will recognize that, in some embodiments, step 420 may be optional in that no determination may be needed, or performed, for determining whether the first device corresponds to a shared device. For example, if the first device is a non-shared device, then upon receipt of the first audio data, communications system 222 may be able to recognize that the device is a non-shared device.

At step 422, speaker identification processing may be performed to the first audio data that was received. For instance, speaker identification system 270 may perform speaker identification processing to the first audio data to determine a speaker of the first message. Speaker identification system 270, for example, may generate a voice print of the first audio data, and then attempt to match the voice print to one or more voice prints stored within memory as being associated with the first device identifier's particular group account. For example, first shared electronic device 100a may have first device identifier 111.xxx, which may be associated with first group account identifier 111.yyy. Speaker identification system 270 may access user accounts system 268 and/or communications accounts system 228 to determine which, if any, voice prints are stored for the first group account associated with the first group account identifier, to determine whether or not those voice prints substantially match the voice print generated for the first audio data.

Speaker identification processing may correspond to one exemplary technique for determining a likely speaker of an utterance received at an electronic device. However, in some embodiments, additional techniques may be employed that may be used with speaker identification processing, or instead of speaker identification processing. In one embodiment, presence data may be received by the first device and/or the computing system (from the first device). The presence data may, for example, indicate that a non-shared device associated with a particular user account is located proximate to the first device. For example, the first device may determine a received signal strength indicator ("RSSI") value, where the RSSI value indicates how strong a communications signal is between the first device and another device. If the RSSI indicator is greater than a predefined RSSI threshold, then that may indicate that a particular device is located substantially nearby the first device. If that device located nearby also corresponds to a particular non-shared device of an individual having a user account associated with the first group account, then that may indicate that the first user is the likely speaker of the utterance. As another example, the first device may employ computer vision processing to determine an identity of individuals located nearby. If a particular individual corresponding to a user account associated with the first group account is identified as being nearby at a substantially same time as when the first audio data is received, then this may indicate that the individual is a speaker of the utterance. Persons of ordinary skill in the art will recognize that additional techniques for determining a speaker associated with received audio data may be employed, and the aforementioned are merely exemplary. Furthermore, in some embodiments, speaker identification processing may be performed by the first device, and information indicating whether or not the speaker was able to be identified may be sent to the computing system (e.g., computing system 200). For example, voice activated electronic device 100a may employ speaker identification processing system 270, and may send information indicating that the speaker of the first audio data was able to be identified, or unable to be identified.

At step 424, a determination is made as to whether or not a speaker has been identifier based on the speaker identification processing performed at step 422. If a speaker has been identified, then process 400 may proceed to step 440 of FIG. 4C. However, if a speaker has not been identified, then process 400 may proceed to step 454 of FIG. 4D.

If, at step 420, it is determined that the first device is not a shared device, then process 400 may proceed to step 426, as seen by FIG. 4B. At step 426, a first user account associated with the first device identifier may be determine. In the illustrative embodiment, if the first device is determine to be a non-shared device at step 420, then the first device may correspond to a personal device. Typically, a personal device would be associated with one particular user account, as it may normally be operated by a single individual. For example, an individual's mobile device (e.g., smartphone, tablet, laptop, etc.) may correspond to an exemplary personal device. Therefore, the particular user account of the individual associated with that particular device may be determined at step 426.

At step 428, first message metadata that indicates that the first message was sent from the first user account may be generated. Communications system 222 may generate metadata to be sent with the first message to the targeted recipient's device(s) that indicates that the first message was sent from the first device. In some embodiments, the first metadata may indicate, amongst other information, a time that the first message was sent, a user account corresponding to the sender of the first message, and a device that the first message was sent from. As an illustrative example, the first metadata may indicate that the message of utterance 4, "Want to have dinner at my place?", was sent from a personal device associated with individual 2.

At step 430, second audio data representing the first message may be generated. For instance, second audio data representing a portion of the utterance that includes the message directed to the targeted recipient may be generated. As an illustrative example, second audio data representing the message: "Want to have dinner at my place?" may be generated by communications system 222. In one embodiment, communications system 222 may provide the message to TTS system 264, which may generate audio data representing the portion of the spoken utterance corresponding to the first message. In some embodiments, an additional message may generated, using the first message metadata, which may preface the first message. For example, the additional message may indicate a sender of the first message such that when a recipient (e.g., individual 12) requests that his/her messages be played using their shared device (e.g., second shared electronic device 100b), then the additional message plays prior to the first message. As an illustrative example, the additional message may correspond to, "You have {Number of Messages} from {Communication Identifier of Sender's User account}." In some embodiments, the first message metadata and the second audio data may be sent to the shared device associated with the recipient. For example, communications system 222 may send the first message notification, indicating that the first message has been received, and the second audio data, which represents the message intended to be sent to the recipient, to the shared device associated with the recipient's group account. For example, individual 12 may be associated with second shared electronic device 100b, and therefore second shared electronic device 100b may receive, from computing system 200, second audio data representing response 16, as well as a notification mechanism for second shared electronic device 100b for indicating to individual 12 that a new message has been received. However, in some embodiments, generation of the second audio data need not occur until a request for message playback has been received from a recipient, and therefore step 430 may be optional.

At step 432, a first message notification for the shared device associated with the targeted recipient may be generated. The first message notification may correspond to any suitable indication that notifies an individual that a message was received. For example, the first message notification may correspond to a command that causes a light ring, or a portion of a light ring, to turn a particular color. As another example, the first message notification may correspond to a graphical user interface ("GUI"), or a portion of a GUI, that will display a visual indicator that a new message has been received. As still yet another example, the first message notification may correspond to any suitable audible or haptic feedback that may be capable of indicating to a recipient that a new message was received. In some embodiments, if the recipient device is a non-shared device, then a similar process may occur in that the first message notification may be generated for the non-shared device.

At step 434, the first message metadata and the second audio data may be stored by the message data store for the second group account, as well as for any user accounts associated with the second group account (e.g., the first user account). For example, the second audio data representing the first message, as well as information corresponding to the message (e.g., the first message metadata) may be stored by message data store 226 for the second group account. Similarly, the second audio data and the first message metadata may be stored by message data store 226 for the first user account. However, the messaging information stored for the first user account may indicate that the message is read, as the message was sent by the first user account.

If, at step 416, it was determined that there are one or more user accounts associated with the second group account, then device identifiers of the personal devices corresponding to the user account(s) may be determined at step 418. For example, each personal device associated with the second group account may correspond to a user account that is able to access communications that have been received by the second group account. In this particular scenario, after step 434, process 400 may also include step 436, where a second message notification for the one or more user accounts may be generated. Furthermore, at step 438, the second message notification may be sent to the personal device(s) associated with the user account(s) associated with the second group account. The second message notification may indicate to each user associated with a particular personal device that a new message has been received for their group account, and may additionally provide one or more mechanisms for allowing that user to access the message using their personal device. For example, if a new message was sent to the recipient's shared electronic device, then a first mobile device, associated with a user account also associated with the second group account, may receive its own message notification indicating that a new message was received. The message notification may, for example, provide text data representing the message, a link (e.g., a uniform resource location ("URL")) for accessing the new message, and/or a visual, audible, and/or haptic notification that a new message was received. As an illustrative example, in response to receiving audio data representing response 16, communications system 222 may determine that one or more user accounts are associated with the same group account as second shared electronic device 100b. For instance, individual 12, as well as one or more additional individuals, may have user accounts that are associated with the second group account of shared electronic device 100b. Communications system 222 may then generate and send a message notification to the additional devices associated with those user accounts so that an individual operating that additional device may also be notified of the newly received message. Persons of ordinary skill in the art will recognize that steps 436 and 438 may be optional, and if a particular group account has no additional devices associated therewith, then steps 436 and 438 may be omitted. Process 400 may then proceed to step 466, which is described in greater detail below.

If, at step 424, a speaker for the first audio data was able to be identified, then process 400 may proceed to step 440. At step 440, a first user account associated with speaker identifier that was determined at step 424 may be determined. For instance, speaker identification system 270 may determine that a speaker of the first audio data representing utterance 4 may correspond to individual 2. In response, communications system 222 may access communications accounts system 228 to determine a user account corresponding to individual 2 that is also linked to the group account identifier for first shared electronic device 100a.

At step 442, first message metadata may be generated to indicate that the first message was sent from the first user account. In some embodiments, step 442 may be substantially similar to step 428, with the exception that at step 442, the first message metadata may indicate that the message was send from the first user account because the message was spoken by the first individual to a first shared device, whereas at step 428, the message is sent from the first user account because the message was received by the first individual's personal device. At step 444, second audio data representing the second message may be generated. In some embodiments, step 444 may be substantially similar to step 430, and the previous description may apply.

At step 446, first message notification for the shared device may be generated. Step 446 may be substantially similar to step 432 with the exception that at step 446, the first message notification may indicate that the first message was spoken by the first individual, and that the first message was sent from the first shared device. At step 448, the first message notification and the second audio data may be stored for the second group account, the first group account, and the first user account, as well as any additional user accounts associated with the first group account, and the first message notification and the second audio data may also be stored for the second group account and any user accounts associated with the second group account.

At step 450, a second message notification may be generated for the user account(s) associated with the second group account determined at step 416. At step 452, the second message notification may be sent to the corresponding personal devices associated with those user accounts. In some embodiments, steps 448, 450, and 452 may be substantially similar to steps 434, 436, and 438, and the previous descriptions may apply. Process 400 may then proceed to step 466, in some embodiments, which is described in greater detail below.

Figure 4A:
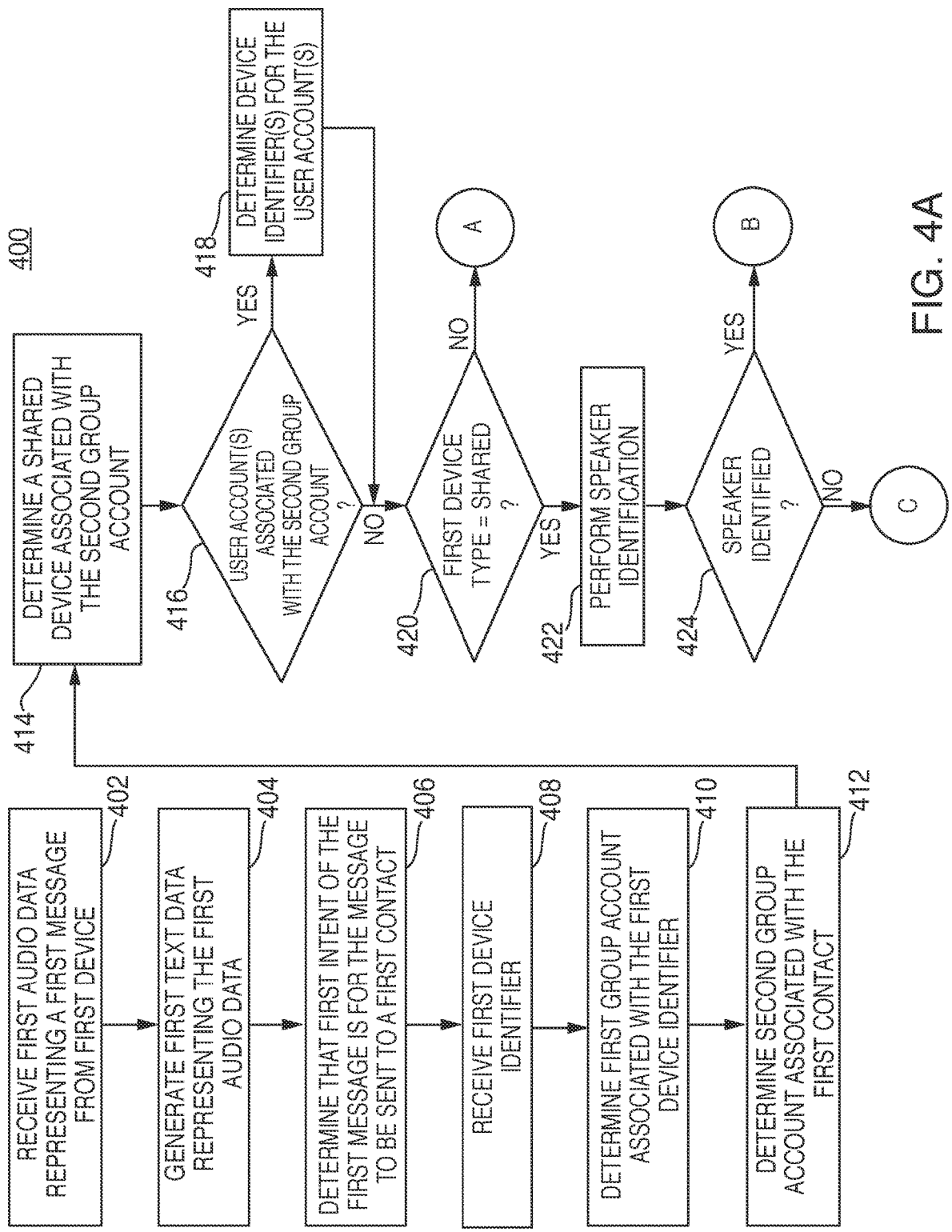
Figure 4D:
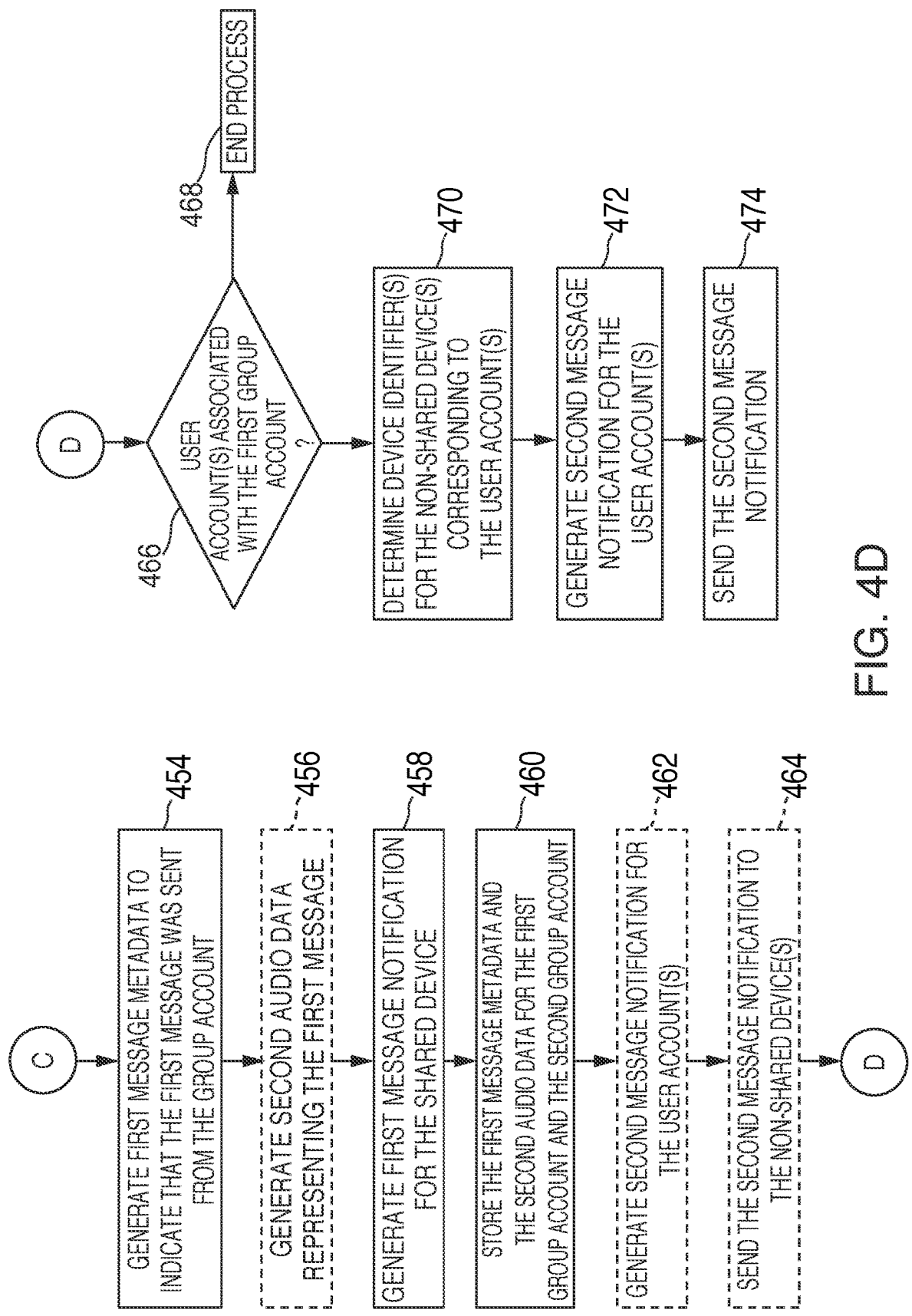

If, at step 424, no speaker was capable of being identified by the speaker identification processing by speaker identification system 270, then process 400 may proceed to step 454 of FIG. 4D. At step 454, first message metadata may be generated that indicates that the first message was sent from the first group account associated with the first device. For example, if the first device was determined to be a shared device, and no speaker was able to be identified for speaking the utterance including the message to be sent to the recipient, then the first message metadata may be generated to indicate that the first message is sent from the first group account. For example, with reference to FIG. 1, the first message metadata may indicate that the message of utterance 4 (e.g., "Want to have dinner at my place?") was sent from first shared electronic device 100a, associated with the first group account having a first communications identifier being "the Jones household." At step 456, second audio data representing the first message may be generated. In some embodiments, step 456 may be substantially similar to step 430, and the previous description may apply.

At step 458, a first message notification for the shared device may be generated. Step 458 may be substantially similar to step 432 with the exception that at step 458, the first message notification may indicate that the first message was sent from the first shared device. At step 460, the first message notification and the second audio data may be stored for the first group account and the second group account. At step 462, a second message notification may be generated for the user accounts associated with the second group account determined at step 416. At step 464, the second message notification may be sent to the personal devices corresponding to those user accounts. In some embodiments, steps 460, 462, and 464 may be substantially similar to steps 434, 436, and 438, and the previous descriptions may apply. Process 400, in some embodiments, may proceed to step 466, which is described in greater detail below.

At step 466, a determination may be made as to whether there are any user accounts associated with the first group account. For example, similarly to the determination made at step 416, any user account also associated with a same group account (e.g., the first group account) as the first device may be determined at step 466. As an illustrative example, individual 2 may possess a mobile device, which may be paired to their particular user account, as well as to the first group account.

If, at step 466, it is determined that there are no user accounts associated with the first group account (e.g., no additional entries into communications table 300 associated with a same group account identifier), then process 400 may proceed to step 468 where process 400 may end. However, if at step 466, one or more user accounts are determined to be associated with the same group account as that of the first device, then process 400 may proceed to step 470. At step 470, device identifier(s) associated with the non-shared device(s) corresponding to the user account(s) linked to the first group account may be determined. For example, if the first group account corresponds to first group account identifier 111.yyy, as seen in FIG. 3, then device identifiers 222.xxx and 333.xxx, corresponding to entries 304 and 306, may be determined to also be associated with that same first group account, as they are associated with one or more user accounts. At step 472, a second message notification for (each of) the user account(s) may be generated. The second message notification(s) may, for instance, be substantially similar to the first message notification of step 454, with the exception that the second message notification(s) may also indicate that a message was sent from the first shared device associated with that personal device's group account. At step 474, the second message notification may be sent to the corresponding non-shared device(s) associated with the user account(s) identified at step 466 as being associated with the same group account as the first device (e.g., the first group account).

Figure 5:
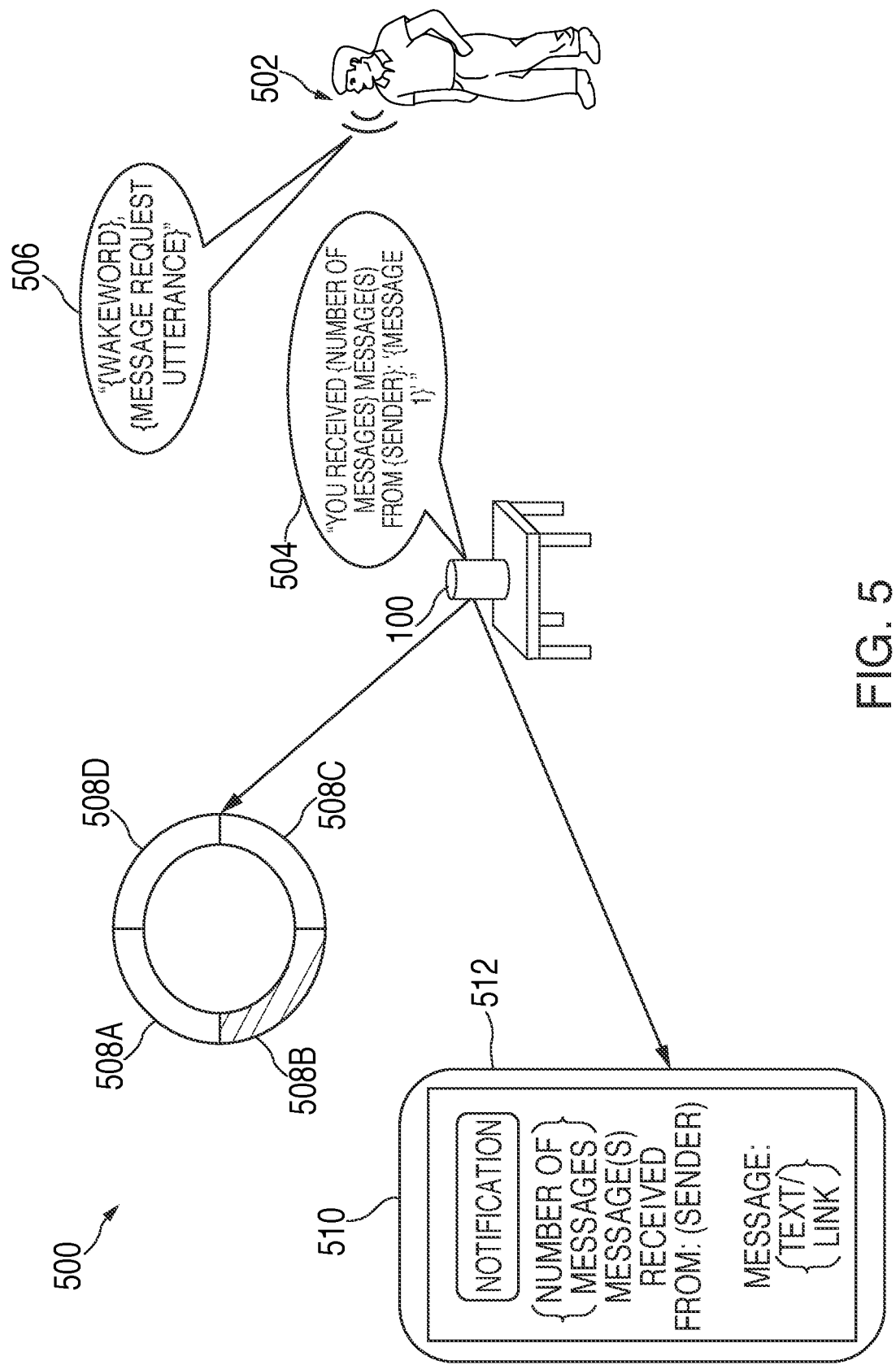
FIG. 5 is an illustrative diagram of another exemplary system for outputting messages and providing message notifications, in accordance with various embodiments.

FIG. 5 is an illustrative diagram of another exemplary system for outputting messages, in accordance with various embodiments. System 500, in one non-limiting embodiment, includes an individual 502, as well as a shared electronic device 100. Electronic device 100 may, for instance, correspond to an exemplary electronic device, such as described previously in FIG. 2. In one embodiment, individual 502 may speak utterance 504 to shared electronic device 100. Utterance 504, for instance, may be of the format, "{Wakeword}, {Message Request Utterance}." In the illustrative embodiment, {Wakeword} may correspond to a wakeword, or trigger expression, for shared electronic device 100, and {Message Request Utterance} may correspond to an exemplary utterance whose intent is for obtaining messages received by a group account associated with electronic device 100, as well as, in particular, for an individual's user account, such as a user account associated with individual 502. As an illustrative example, {Wakeword} may be "Alexa," and {Message Request Utterance} may be "Do I have any messages?" or "Play my messages."

Upon determining that the wakeword was uttered, shared electronic device 100 may begin sending audio data representing utterance 504 to computing system 200 and, in particular, speech-processing system 250. For instance, upon receiving the audio data, ASR system 258 may generate text data representing the audio data, and NLU system 260 may determine an intent of utterance 504 using that text data. In one embodiment, NLU system 260 may determine that the intent of utterance 504 is for messages to be played using shared electronic device 100.

In response to determining that the intent of utterance 504 is for messages to be played, communications system 222 may first attempt to determine an account on computing system 200 whose message are to be retrieved, and potentially output. In one embodiment, a device identifier associated with shared electronic device 100 may be received by computing system 200, and a group account identifier corresponding to the device identifier may be determined so that a group account of shared electronic device 100 may be obtained. For example, using communications table 300, a group account identifier associated with the received device identifier of shared electronic device 100 may be determined. Using the group account identifier, the corresponding group account stored by communications accounts system 228 may be determined, and the messages (if any) received for that group account may be obtained.

In some embodiments, upon receiving audio data representing utterance 504, speaker identification system 270 may attempt to determine a speaker of utterance 504. For instance, speaker identification system 270 may generate a voice print of the audio data, and may attempt to match the voice print to one or more stored voice prints from user accounts module 268. In one embodiment, the device identifier associated with shared electronic device 100 may be employed to narrow the search of voice prints to those voice prints corresponding to the group account associated with the group account identifier determined for the device identifier of shared electronic device 100. If speaker identification system 270 is able to determine the speaker of utterance 504 (e.g., individual 2), then messages for the speaker may also be received, as well as any messages for the group account. However, persons of ordinary skill in the art will recognize that this is merely exemplary, and in some embodiments, each individual's user account associated with a group account may be capable of receiving all messages sent to any user account associated with that group account.

After receiving the messages from the corresponding group account of shared electronic device 100, communications system 222 may send the messages to TTS system 264 to generate audio data representing a response indicating the messages, as well as indicating a number of messages that have been received, and from whom those messages were received from. For instance, response 506 may be, "You received {Number of Messages} message(s) from {Sender}: '{Message 1}.'" As an illustrative example, if one message was sent to the group account associated with electronic device 100 from another shared electronic device associated with a particular group account, then response 506 may be, "You received one message from the Jones household," which may be followed by the particular message that was sent. If multiple messages were received from a same sender, then each message may be played one after another. However, if different messages were received from different senders, then the individual (e.g., individual 502) may decide how he/she would like those messages to be consumed (e.g., play messages from first sender first, followed by the messages from the second sender, etc.).

In some embodiments, when a message is received for a group account, and/or for a particular user account associated with a group account, a notification may be provided to the shared electronic device of that group account indicating that a new message was received. In one embodiment, shared electronic device 100 may include a light ring separated into four portions, portions 508*a-d*. When a new message is received, communications system 222 may generate and send a message notification that, upon receipt, causes one or more of the four portions to become illuminated. For example, when a new message is received, communications system 222 may send a communication to shared electronic device 100 that causes light ring portion 508*b* to illuminate a first color.

In some embodiments, different individuals associated with shared electronic device 100, cause different light ring portions to become illuminated. For example, messages received for a first individual may cause light ring portion 508*a* to become illuminated, whereas messages received for a second individual may cause light ring portion 508*b* to become illuminated. However, persons of ordinary skill in the art will recognize that any suitable light ring portion, or portions, may illuminated in any suitable manner (e.g., color, intensity, pattern) for any particular individual, and the aforementioned is merely exemplary.

In some embodiments, shared electronic device 100 may include display screen 212. In this particular scenario, communications system 222 may generate and send a visual message notification indicating that a new message, or messages were received for the group account associated with shared electronic device 100. For instance, a GUI including a visual indicator of the received message(s) may be generated and sent to shared electronic device 100 such that display screen 212 is caused to render the GUI. In some embodiments, text data representing the audio data may also be sent to shared electronic device 100 so that the words corresponding to the message may be viewable by individual 502. In this particular scenario, ASR system 258, and STT system 266 may generate text data representing the audio data of the received message(s), and may send that text data to shared electronic device 100 or for being displayed by a GUI rendered by display screen 212. In some embodiments, communications system 222 may, alternatively, generate and send a hyperlink (e.g., a URL) with which the audio data representing the messages and/or the text data may be viewable from. Persons of ordinary skill in the art will further recognize that any suitable mechanism for notifying an individual operating electronic device 100 may be employed for indicating that a message, or messages, have been received, including, but not limited to, visual notifications (e.g., lights of a particular color, blinking lights, certain lights being illuminated), audible notifications (e.g., audible tones), and/or haptic notifications (e.g., vibrating mechanisms).

As mentioned previously, one or more personal devices also associated with the group account may receive notification that a new message, or messages, have been received by the group account and/or by another user account associated with the group account. In some embodiments, system 500 may include a personal device 510 including a display screen 512. Personal device 510 and display screen 512, in one embodiment, may be substantially similar to electronic device 100 and display screen 212, and the previous description may apply with the exception that personal device 510 may correspond to a non-shared device. In response to a message being received for the group account associated with electronic device 100, communications system 222 may generate and send a message notification to personal device 510. For example, the message notification may include a GUI to be displayed by display screen 512 that indicates that a new message (or messages) have been received, the number of messages received, who the messages where received from, as well as text data representing the message(s) and/or a link to access the text data, audio data representing the message(s), and/or image/video data associated with the message(s). In some embodiments, the message notification may be a pop-up message displayed on display screen 512. Further still, one or more audible notifications and/or haptic notifications may be provided to personal device 510 to indicate to an individual operating personal device 510 that a message has been received for their group account and/or personal user account.

FIG. 6 is an illustrative flowchart of an exemplary process for causing messages to be output from a first device, in accordance with various embodiments. Process 600, in a non-limiting embodiment, may begin at step 602. At step 602, first audio data representing a first request may be received from a first device. For example, an individual may request that any messages associated with their user account and/or group account be played. As another example, an individual may ask if he/she has any new messages. As an illustrative example, an individual may speak an utterance, "Alexa, Do I have any new messages?" or "Alexa, play my messages." In response to detecting the wakeword (e.g., "Alexa"), the first device may begin sending audio data representing the spoken request to computing system 200, and in particular speech-processing system 250. However, in some embodiments, a particular sound may be output that causes the first device to begin communicating the first audio data to computing system 200, or a manual input (e.g., pressing a button, touching a touch screen, etc.) may be detected by the first device, which may cause the first device to begin sending audio data representing the first request to computing system 200.

At step 604, first text data representing the first audio data may be generated. In some embodiments, upon receiving the first audio data, computing system 200 may provide the first audio data to speech-processing system 250, which may use ASR system 258 to generate first text data representing the first audio data. At step 606, NLU system 260 may determine that a first intent of the first request is for a message, or messages, to be played. For instance, the first device may have received a message notification, such as a blinking light, an audible tone, or a visual message displayed on a display screen, that indicates that one or more new messages have been received for a group account and/or a user account associated with the group account.

At step 608, a first device identifier corresponding to the first device may be received by communications system 222 of computing system 200. For instance, the first device identifier may correspond to a MAC address, a serial number, an IP address, or any other suitable identification means. At step 610, a first group account associated with the first device identifier may be determined. In some embodiments, communications system 222 may access a communications table, such as communications table 300, to determine an entry corresponding to the received device identifier of the first device. Based on the entry in the communications table, a group account identifier, corresponding to a group account registered and stored by communications accounts system 228, may be determined for the first device. In some embodiments, steps 608 and 610 of FIG. 6 may be substantially similar to steps 408 and 410 of FIG. 4, and the previous descriptions may apply.

At step 612, speaker identification processing may be performed to the received first audio data. For instance, speaker identification system 270 may receive the first audio data, or a copy of the first audio data, and may generate a voice print of the first audio data. Using the generated voice print, a comparison may be made against any stored voice prints for the identified group account. For instance, the first group account may include one or more stored voice prints corresponding to voice biometric information associated with one or more registered users of the first group account. The generated voice print may be compared against the registered users' voice prints to determine whether a voice that spoke the first request substantially matches a voice of one of that group account's users. At step 614, a determination may be made as to whether or not a speaker has been identified, based on the speaker identification processing that was performed.

If, at step 614, it is determined that a speaker has positively been identifier (e.g., a match between the generated voice print and one of the stored voice prints is in excess of a predefined confidence threshold), then process 600 may proceed to step 616. At step 616, a user account associated with the identifier speaker of the first audio data may be determined. In some embodiments, a group account may itself be associated with one or more user accounts. For example, a household's shared electronic device (e.g., electronic device 100) may itself be associated with a group account for that household. Each individual living at the household may then also have their own user account stored by accounts system 268, which may also be linked to the household's group account, which may also be stored by communications accounts system 228 (as well as accounts system 268). Therefore, in response to determining the first group account associated with the first device, and positively identifying a speaker from the first audio data, a user account associated with the individual who spoke the first request may be determined.

At step 618, messages that have been received for the first group account and the user account may be determined. In some embodiments, message data store 226 may be accessed to obtain any messages that have been received for that user account. For example, as described previously, each group account and associated user account may have a corresponding identifier (e.g., group account identifier, user account identifier), with which message may be stored and indexed with. Upon determining that messages are to be received for a particular user account, that user account's identifier, and a group account that that user account is associated with, may be determined, and message data store 226 may be accessed to receive messages that have been stored for that group account identifier and/or user account identifier.

At step 620, second audio data representing the message(s) received for that user account may be generated. In some embodiments, the second audio data that is generated may include the messages that have been received, as well as an introductory message that indicates information associated with each of the messages. For example, the second audio data may include a message indicating a number of messages that have been received, as well as who those messages were received from. Following this information, in one embodiment, may be the messages that have been received. If, for instance, the one or more of the messages are video messages, then an audio portion of the video may be sent (if the requesting device does not include video displaying components). In some embodiments, in addition to generating the second audio data representing the messages, text data representing the messages may also be generated. For example, text data representing the audio message may be generated upon receipt by speech-processing system 250, and the text data may also be stored by message data store 226 for that recipient's user account. At step 622, the second audio data may be sent to the first device that requested the messages.

At step 624, a message read notification may be generated for the first device, as well as for any additional device(s) associated with the first group account. The message read notification generated for the first device may indicate to communications system 222, and particularly message data store 226, that that particular user account associated with the first device has read (heard, viewed, etc.) the messages associated with that user account. These messages may include all messages received for that user account, as well as all messages received for the group account that the user account is associated with. The message read notification for the additional devices associated with that user account may cause any additional devices associated with that user account (e.g., a personal device or devices) to no longer indicate that a new message has been received, so that the corresponding individual does not believe that there are additional messages received upon viewing their personal device(s). For example, if an individual receives the messages for their user account on their shared electronic device, then the message read notification may be generated so that that individual's mobile device no longer shows that those messages have not been "read." At step 626, the message read notification may be sent to the corresponding additional devices associated with the user account.

If, however, at step 614, a speaker was not able to be identified by speaker identification system 270, then process 600 may proceed to step 628. At step 628, messages received for the first group account may be determined. For example, communications system 222 may access message data store 226 and may obtain any messages that have been received for the indicated group account's identifier. At step 630, second audio data representing the messages received may be generated. In some embodiments, the second audio data that is generated may include an introductory message indicating a number of messages that have been received, as well as who those messages were received from. At step 632, the second audio data may be sent to the first device. Steps 628, 630, and 632, in one embodiment, may be substantially similar to steps 618, 620, and 622, with the exception that at steps 628, 630, and 632, the messages that are received are solely associated with the first group account.

At step 634, a message read notification may be generated for the first group account. The message read notification may indicate that the messages associated with that first group account have been received by the first device, and that those messages are no longer new, or, more generally speaking, are not un-read messages. Upon generating the message read notification, message data store 226 may update that status of the messages associated with that group account to be indicated as have been read such that future requests for messages indicate to the recipient that those messages have previously been read.

The various embodiments of the invention may be implemented by software, but may also be implemented in hardware, or in a combination of hardware and software. The invention may also be embodied as computer readable code on a computer readable medium. The computer readable medium may be any data storage device that may thereafter be read by a computer system.

The above-described embodiments of the invention are presented for purposes of illustration and are not intended to be limiting. Although the subject matter has been described in language specific to structural feature, it is also understood that the subject matter defined in the appended claims is not necessarily limited to the specific features described. Rather, the specific features are disclosed as illustrative forms of implementing the claims.

What is claimed is:

1. A computer-implemented method, comprising:
   receiving first audio data representing an utterance detected by a first device, wherein the first device is associated with a plurality of user accounts;
   determining that the first audio data represents a communication that is intended for a recipient;
   generating first communication data corresponding to the communication;
   performing speaker identification processing using the first audio data to determine, from the plurality of user accounts, a first user account associated with a speaker of the utterance;
   generating metadata indicating a sender of the communication;
   based at least in part on determination of the first user account associated with the speaker of the utterance, selecting the first user account to associate with the metadata; and
   causing the first communication data and the metadata to be sent to at least one second device associated with the recipient.

2. The computer-implemented method of claim 1, further comprising determining the first audio data includes a representation of a wakeword.

3. The computer-implemented method of claim 1, further comprising:
   determining the at least one second device based at least in part on a second user account associated with the recipient.

4. The computer-implemented method of claim 1, further comprising determining, using the metadata, a name associated with the first user account.

5. The computer-implemented method of claim 4, further comprising:
   performing text-to-speech processing using the metadata to determine output audio data including a representation of the name; and
   sending the output audio data to the at least one second device.

6. The computer-implemented method of claim 1, further comprising:
   determining the first device is a shared device associated with the first user account and a second account; and
   in response to the speaker identification processing using the first audio data to determine the first user account is associated with the speaker of the utterance, refraining from associating the metadata with the second account.

7. The computer-implemented method of claim 1, further comprising:
   determining the plurality of user accounts comprises at least the first user account; and
   determining voice print data associated with the first user account,
   wherein performing the speaker identification processing comprises processing the first audio data with respect to the voice print data.

8. The computer-implemented method of claim 1, further comprising:
   determining the at least one second device is a shared device; and
   causing the at least one second device to output an indication of the recipient.

9. The computer-implemented method of claim 8, wherein the indication comprises an audio indication and the method further comprises:
   causing playback of the indication;
   after causing playback of the indication, receiving a request to receive the communication; and
   after receiving the request, causing the at least one second device to output a representation of the communication.

10. The computer-implemented method of claim 8, wherein the indication comprises a visual indication and the method further comprises:
    causing output of the indication;
    after causing output of the indication, receiving a request to receive the communication; and
    after receiving the request, causing the at least one second device to output a representation of the communication.

11. A system comprising:
    at least one processor; and
    at least one memory comprising instructions that, when executed by the at least one processor, cause the system to:
    receive first audio data representing an utterance detected by a first device, wherein the first device is associated with a plurality of user accounts;
    determine that the first audio data represents a communication that is intended for a recipient;
    generate first communication data corresponding to the communication;
    perform speaker identification processing using the first audio data to determine, from the plurality of user accounts, a first user account associated with a speaker of the utterance;
    generate metadata to indicate a sender of the communication;
    based at least in part on determination of the first user account associated with the speaker of the utterance, select the first user account to associate with the metadata; and
    cause the first communication data and the metadata to be sent to at least one second device associated with the recipient.

12. The system of claim 11, wherein the at least one memory further comprises instructions that, when executed by the at least one processor, further cause the system to:
    determine a representation of a wakeword.

13. The system of claim 11, wherein the at least one memory further comprises instructions that, when executed by the at least one processor, further cause the system to:
    determine the at least one second device based at least in part on a second user account associated with the recipient.

14. The system of claim 11, wherein the at least one memory further comprises instructions that, when executed by the at least one processor, further cause the system to:
    determine, using the metadata, a name associated with the first user account.

15. The system of claim 14, wherein the at least one memory further comprises instructions that, when executed by the at least one processor, further cause the system to:
perform text-to-speech processing using the metadata to determine output audio data including a representation of the name; and
send the output audio data to the at least one second device.

16. The system of claim 11, wherein the at least one memory further comprises instructions that, when executed by the at least one processor, further cause the system to:
determine the first device is a shared device associated with the first user account and a second user account; and
in response to the speaker identification processing using the first audio data to determine the first user account is associated with the speaker of the utterance, refrain from associating the metadata with the second user account.

17. The system of claim 11, wherein the at least one memory further comprises instructions that, when executed by the at least one processor, further cause the system to:
determine the plurality of user accounts comprises at least the first user account; and
determine voice print data associated with the first user account,
wherein the instructions that cause the system to perform the speaker identification processing comprise instructions that, when executed by the at least one processor, cause the system to process the first audio data with respect to the voice print data.

18. The system of claim 11, wherein the at least one memory further comprises instructions that, when executed by the at least one processor, further cause the system to:
determine the at least one second device is a shared device; and
cause the at least one second device to output an indication of the recipient.

19. The system of claim 18, wherein the indication comprises an audio indication and wherein the at least one memory further comprises instructions that, when executed by the at least one processor, further cause the system to:
cause playback of the indication;
after causing playback of the indication, receive a request to receive the communication; and
after receipt of the request, cause the at least one second device to output a representation of the communication.

20. The system of claim 18, wherein and wherein the at least one memory further comprises instructions that, when executed by the at least one processor, further cause the system to:
cause output of the indication;
after causing output of the indication, receive a request to receive the communication; and
after receipt of the request, cause the at least one second device to output a representation of the communication.

* * * * *